United States Patent
Bossenmaier et al.

(10) Patent No.: US 7,235,574 B2
(45) Date of Patent: Jun. 26, 2007

(54) PENTAFLUOROSULFANYL COMPOUNDS

(75) Inventors: Birgit Bossenmaier, Seefeld (DE); Walter-Gunar Friebe, Mannheim (DE); Guy Georges, Habach (DE); Matthias Rueth, Penzberg (DE); Edgar Voss, Bichl (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 110 days.

(21) Appl. No.: 11/073,227

(22) Filed: Mar. 4, 2005

(65) Prior Publication Data

US 2005/0197370 A1 Sep. 8, 2005

(30) Foreign Application Priority Data

Mar. 5, 2004 (EP) .................... 04005275

(51) Int. Cl.
*A61K 31/422* (2006.01)
*C07D 413/02* (2006.01)

(52) U.S. Cl. .................... 514/374; 548/235
(58) Field of Classification Search ........... 514/374; 548/235

See application file for complete search history.

(56) References Cited

U.S. PATENT DOCUMENTS

| | | | |
|---|---|---|---|
| 2005/0124670 A1* | 6/2005 | Bossenmaier et al. | 514/359 |
| 2005/0203064 A1* | 9/2005 | Bossenmaier et al. | 514/79 |
| 2005/0203604 A1* | 9/2005 | Bossenmaier et al. | 514/79 |
| 2006/0069095 A1* | 3/2006 | Hofmeister et al. | 514/235.2 |
| 2006/0116407 A1* | 6/2006 | Bossenmaier et al. | 514/370 |
| 2006/0211750 A1* | 9/2006 | Friebe et al. | |

FOREIGN PATENT DOCUMENTS

| | | |
|---|---|---|
| EP | 1270571 | 1/2003 |
| WO | WO 98/03505 | 1/1998 |
| WO | WO 01/77107 | 10/2001 |
| WO | WO 03/031442 | 4/2003 |

OTHER PUBLICATIONS

Database Caplus 'Online! American Chemical Society, Columbus, Ohio; US; Feb. 27, 2004, XP002291292 retrieved from STN Database accession No. 2004:159301 *abstract* & JP 2004 059452 A (Asahi Glass Co Ltd) Feb. 26, 2004.
Wilks et al., Progress in Growth Factor Research, 2, pp. 97-111 (1990).
Chan et a., Cur. Opin. in Immunol., 8, pp. 394-401 (1995).
Yarden et al., Ann. Rev. Biochem., 57, pp. 443-478 (1988).
Wright et al., Br. J. Cancer, 65, pp. 118-121 (1992).
Baselga et al., Oncology, 63 (Suppl. 1), pp. 6-16 (2002).
Ranson et al., Oncology, 63 (Suppl. 1), pp. 17-24 (2002).

* cited by examiner

*Primary Examiner*—Kamal A. Saeed
*Assistant Examiner*—Nyeemah Grazier
(74) *Attorney, Agent, or Firm*—George W. Johnston; Dennis P. Tramaloni; Brian C. Remy

(57) ABSTRACT

The present invention provides the compounds of formula I-A formula I-A

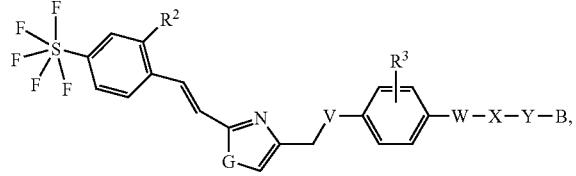

their pharmaceutically acceptable salts or esters, enantiomeric forms, diastereoisomers and racemates, the preparation of the above-mentioned compounds, pharmaceutical compositions containing them and their manufacture, as well as the use of the above-mentioned compounds in the control or prevention of illnesses such as cancer.

15 Claims, No Drawings

PENTAFLUOROSULFANYL COMPOUNDS

PRIORITY TO RELATED APPLICATIONS

This application claims the benefit of European Application No. 04005275.5, filed Mar. 5, 2004, which is hereby incorporated herein by reference in its entirety.

FIELD OF THE INVENTION

The present invention relates to novel arylazole derivatives, to a process for their manufacture, pharmaceutical compositions containing them and their manufacture as well as the use of these compounds as pharmaceutically active agents for the prevention or treatment of cancer.

BACKGROUND OF THE INVENTION

Protein tyrosine kinases (PTKs) catalyze the phosphorylation of tyrosyl residues in various proteins involved in the regulation of cell growth and differentiation (Wilks et al., Progress in Growth Factor Research 97 (1990) 2; Chan, A. C., and Shaw, A. S., Curr. Opin. Immunol. 8 (1996) 394–401). Such PTKs can be divided into receptor tyrosine kinases (e.g. EGFR/HER-1, c-erB2/HER-2, c-met, PDGFr, FGFr) and non-receptor tyrosine kinases (e.g. src, lck). It is known that many oncogenes encode proteins which are aberrant tyrosine kinases capable of causing cell transformation (Yarden, Y., and Ullrich, A., Annu. Rev. Biochem. 57 (1988) 443–478; Larsen et al., Ann. Reports in Med. Chem., 1989, Chpt. 13). Also over-expression of a normal proto-oncogenic tyrosine kinase may result in proliferative disorders.

It is known that receptor tyrosine kinases of the HER-family like HER-2 and EGFR (HER-1) are frequently aberrantly expressed in common human cancers such as breast cancer, gastrointestinal cancer such as colon, rectal or stomach cancer, leukemia and ovarian, bronchial and pancreatic cancer. High levels of these receptors correlate with poor prognosis and response to treatment (Wright, C., et al., Br. J. Cancer 65 (1992) 118–121).

Accordingly, it has been recognized that inhibitors of receptor tyrosine kinases are useful as selective inhibitors of the growth of mammalian cancer cells. Therefore several small molecule compounds as well as monoclonal antibodies are in clinical trials for the treatment of various types of cancer (Baselga, J., and Hammond, L. A., Oncology 63 (Suppl. 1) (2002) 6–16; Ranson, M., and Sliwkowski, M. X., Oncology 63 (Suppl. 1) (2002) 17–24).

Some substituted oxazoles are known in the art. WO 98/03505, EP 1 270 571, WO 01/77107, WO 03/031442 and WO 03/059907 disclose related heterocyclic compounds as—tyrosine kinase inhibitors.

However there remains a need for new compounds with improved therapeutic properties, such as enhanced activity, higher metabolic stability and improved pharmacokinetic properties to name only a few.

SUMMARY OF THE INVENTION

The present invention relates to new compounds of the general formula I-A, formula I-A wherein:

$R^2$ is hydrogen or fluorine;
$R^3$ is hydrogen, $(C_1-C_3)$alkyl, $(C_1-C_3)$alkoxy, or halogen;
G is —NH—, —S—, or —O—;
V is —O—, —NH—, —C(O)—NH—, —NH—C(O)—, or —S(O)$_x$—;
W is —CH$_2$— or a direct bond;
X is —NH—, —O—, —S(O)$_x$—, —C(O)—, —C(O)NH—, —NHC(O)—, —S(O)$_2$NH—, —NHS(O)$_2$—, —CH=CH—, —C≡C—, or —CH$_2$—;
Y is —(CH$_2$)$_n$—;
B is selected from the group consisting of:
  (a) imidazolyl; which is:
    (1) unsubstituted; or
    (2) once substituted with —C(O)OH; or
    (3) one, two or three times substituted with alkyl, which alkyl is:
      (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
      (B) unsubstituted or one, two or three times substituted with —OH, —NH$_2$, —C(O)OH, or —P(O)(CH$_3$)$_2$; or
    (4) once substituted with —C(O)OH and one, two or three times substituted with alkyl, which alkyl is:
      (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
      (B) unsubstituted or one, two or three times substituted with —OH, —NH$_2$, —C(O)OH, or —P(O)(CH$_3$)$_2$;
  (b) pyrazolyl; which is:
    (1) unsubstituted; or
    (2) once substituted with —C(O)OH; or
    (3) one, two or three times substituted with alkyl, which alkyl is:
      (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
      (B) unsubstituted or one, two or three times substituted with —OH, —NH$_2$, —C(O)OH, or —P(O)(CH$_3$)$_2$; or (4) once substituted with —C(O)OH and one, two or three times substituted with alkyl, which alkyl is:
   (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
   (B) unsubstituted or one, two or three times substituted with —OH, —NH$_2$, —C(O)OH, or —P(O)(CH$_3$)$_2$;
(c) triazolyl; which is:
   (1) unsubstituted; or
   (2) once substituted with —C(O)OH; or
   (3) one, two or three times substituted with alkyl, which alkyl is:
      (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
      (B) unsubstituted or one, two or three times substituted with —OH, —NH$_2$, —C(O)OH, or —P(O)(CH$_3$)$_2$; or
   (4) once substituted with —C(O)OH and one, two or three times substituted with alkyl, which alkyl is:
      (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
      (B) unsubstituted or one, two or three times substituted with —OH, —NH$_2$, —C(O)OH, or —P(O)(CH$_3$)$_2$; and
(d) tetrazolyl, which is:
   (1) unsubstituted; or
   (2) once substituted with —C(O)OH; or
   (3) one, two or three times substituted with alkyl, which alkyl is:
      (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
      (B) unsubstituted or one, two or three times substituted with —OH, —NH$_2$, —C(O)OH, or —P(O)(CH$_3$)$_2$; or
   (4) once substituted with —C(O)OH and one, two or three times substituted with alkyl, which alkyl is:
      (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and (B) unsubstituted or one, two or three times substituted with —OH, —NH$_2$, —C(O)OH, or —P(O)(CH$_3$)$_2$; and n is 1, 2 or 3; and
x is 0, 1 or 2; and pharmaceutically acceptable salts or esters thereof.

The compounds of formula I-A are useful for preventing or treating proliferative diseases and conditions such as tumor growth and cancer including, but not limited to, breast cancer, leukemia, ovarian cancer, bronchial or lung cancer, pancreatic cancer, and gastrointestinal cancer such as colon cancer, rectal cancer, and stomach cancer.

The compounds of the present invention show activity as inhibitors of the HER-signaling pathway and therefore possess anti-proliferative activity. The present invention provides the compounds of formula I-A and their pharmaceutically acceptable salts or esters, enantiomeric forms, diastereoisomers and racemates, the preparation of the above-mentioned compounds, compositions containing them and their manufacture as well as the use of the above-mentioned compounds in the control or prevention of illnesses, especially of illnesses and disorders as mentioned above or in the manufacture of corresponding pharmaceutical compositions.

DETAILED DESCRIPTION OF THE INVENTION

As used herein, the term "(C$_1$–C$_3$)alkyl" means a linear or branched, saturated hydrocarbon with 1, 2 or 3 carbon atoms. Examples are methyl, ethyl, propyl or isopropyl.

As used herein, the term "(C$_1$–C$_3$)alkoxy" means a (C$_1$–C$_3$)alkyl group as defined above, which is attached via an oxygen-atom (i.e., —O-alkyl such as methoxy, ethoxy, etc.).

As used herein, the term "alkyl" denotes a linear or branched, saturated hydrocarbon with 1 to 6, preferably 1 to 4 and more preferably 1 or 2 carbon atoms. Preferred "alkyl" groups are methyl, ethyl, propyl, isopropyl, n-butyl, 2-butyl, tert-butyl and the like. Preferred substituted "alkyl" groups are for example 2-(2-hydroxyethoxy)ethyl, 1-hydroxyethyl, 2-hydroxyethyl, 2-(2-methoxy-ethoxy)-ethyl, hydroxymethyl, 2-methanesulfinyl-ethyl, 2-methanesulfonyl-ethyl, dimethyl-phosphinoylmethyl, methoxymethyl, carboxymethyl, 2-carboxyethyl, aminomethyl, 1-aminoethyl, 2-aminoethyl and the like. In addition, the present invention provides alkyls which may optionally be interrupted one, two or three times by —O—, S(O)$_x$—, —S(O)$_2$NH$_2$—, —NH$_2$S(O)$_2$—, or —P(O)(CH$_3$)— and may be unsubstituted or one, two or three times substituted with —OH, —NH$_2$, —C(O)OH or —P(O)(CH$_3$)$_2$.

The imidazole, pyrazole, triazole or tetrazole rings may be attached to the group —W—X—Y— of formula I-A via any suitable carbon- or nitrogen atom. They may further be unsubstituted, once substituted by —C(O)OH and/or one, two or three times substituted with "alkyl". Examples are 1H-[1,2,3]triazol-1-yl; 1H-[1,2,3]triazol-5-yl; 1H-imidazol-1-yl; 1H-tetrazol-5-yl; 2-(2-hydroxyethyl)-1H-imidazol-1-yl; 2-(2-aminoethyl)-1H-imidazol-1-yl; 2-ethoxyethyl-1H-imidazol-1-yl; 2-[2-(Dimethyl-phosphinoyl)-ethyl]-1H-imidazol-1-yl and the like.

As used herein, the term "halogen" denotes fluorine, chlorine, bromine and iodine, preferably fluorine or chlorine.

As used herein the term "proliferative disease" means a cell proliferative disease such as an inflammatory disease (e.g., rheumatoid arthritis) or in particular, oncological diseases such as, but not limited to, tumor growth or cancer including breast cancer, leukemia, ovarian cancer, bronchial or lung cancer, pancreatic cancer, and gastrointestinal cancer such as colon cancer, rectal cancer, and stomach cancer.

As used herein, when referring to the receptor tyrosine kinases of the HER-family like HER-2 and EGFR (HER-1), the acronym "HER" refers to human epidermal receptor and the acronym "EGFR" refers to epidermal growth factor receptor.

As used herein, "THF" refers to tetrahydrofuran

As used herein, the term "DMF" refers to N,N-dimethylformamide.

As used herein, the term "r.t." refers to room temperature.

As used herein, the term "FCS" refers to Fetal Calf Serum.

As used herein, the term "EGTA" refers to Ethylene glycol-bis(2-aminoethylether)-N,N,N',N'-tetraacetic acid.

As used herein, the term "Hepes" refers to 4-(2-hydroxyethyl)-1-piperazineethanesulfonic acid.

As used herein, the term "PMSF" refers to Phenylmethylsulfonyl fluoride.

As used herein, the term "Aprotinin" refers to a naturally occurring protein that is obtained and purified from cow's lungs.

As used herein, the term "Orthovanadate" refers to $Na_3VO_4$.

As used herein, the term "DMSO" refers to N,N-dimethylsulfoxide.

As used herein, the term "pY 1248" refers to the phosphorylated tyrosine residue 1248 of human epidermal receptor 2.

As used herein, "NSCLC cells" (e.g. QG56, A549, Calu-3) refers to Non-Small-Cell Lung Cancer.

As used herein, the term "NCI" refers to the National Cancer Institute.

As used herein, "Lactose Anhydrous DTG" refers to anhydrous lactose in direct tabletting grade.

As used herein, in relation to mass spectrometry (MS) the term "ESI+" refers to positive electrospray ionization mode; the term "APCI+" and "APCI−" refer to positive and negative atmospheric pressure chemical ionization mode and the term "M+" refers to the positive molecular mass ion peak of the ionized molecule.

As used herein, in relation to nuclear magnetic resonance (NMR) the term "$D_6$-DMSO" refers to deuterated N,N-dimethylsulfoxide and the term "$CDCl_3$" refers to deuterated chloroform.

As used herein, the term "Triton" refers to octylphenol ethoxylate.

As used herein, the term "DMPU" refers to 1,3-Dimethyl-3,4,5,6-tetrahydro-2(1H)-pyrimidinone.

As used herein, the term "LC-MS" refers to liquid chromatography-mass spectrometry.

As used herein, the term "HPLC-MS" refers to high-performance liquid chromatography-mass spectrometry.

As used herein, the term "content according to GC/FID" refers to the purity according a measurement with gas chromatography with a flame ion detector.

As used herein, the term "a therapeutically effective amount" of a compound means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I-A and are formed from suitable non-toxic organic or inorganic acids or organic or inorganic bases.

Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and quaternary ammonium hydroxides, such as for example, tetramethylammonium hydroxide. The chemical modification of a pharmaceutical compound (i.e. a drug) into a salt is a technique well known to pharmaceutical chemists to obtain improved physical and chemical stability, hygroscopicity, flowability and solubility of compounds. See Bastin, R. J. et al, Organic Proc. Res. Dev. 4 (2000) 427–435.

Preferred examples for the group —W—X—Y— are:
—$(CH_2)_4$—; —O—$(CH_2)_3$—; —C(O)—$(CH_2)_3$—;
—S—$(CH_2)_3$—; —$S(O)_2$—$(CH_2)_3$—;
—S(O)—$(CH_2)_3$—; —$S(O)_2$—NH—$(CH_2)_2$—; —NH—C(O)—$(CH_2)_2$—; —C(O)—NH—$(CH_2)_2$—;
—$CH_2$—NH—$(CH_2)_2$—; —$CH_2$—O—$(CH_2)_2$—;
—$CH_2$—S(O)—$(CH_2)_2$—; —$CH_2$—$S(O)_2$—$(CH_2)_2$—;
—CH═CH—$CH_2$—; —CH═CH—$(CH_2)_2$—; —$CH_2$—CH═CH—$CH_2$—; or —C≡C—$(CH_2)_2$—.

A preferred embodiment of the present invention are the compounds of formula I-A, wherein:
$R^2$ is fluorine;
G is —S— or —O—;

and the remaining substituents have the meaning given above for formula I-A.

Another preferred embodiment of the present invention are the compounds of formula I-A, wherein:
$R^2$ is hydrogen;
G is —S—;

and the remaining substituents have the meaning given above for formula I-A.

Another preferred embodiment of the present invention are the compounds of formula I-A, wherein:
$R^2$ and $R^3$ are both hydrogen;
V and G are both —O—;
—W—X—Y— is —$(CH_2)_4$—;
B is selected from the group consisting of:
  (a) imidazolyl; which is:
    (1) unsubstituted; or
    (2) once substituted with —C(O)OH; or
    (3) one, two or three times substituted with alkyl, which alkyl is:
      (A) optionally interrupted one, two or three times by —O—, —$S(O)_x$—, —$S(O)_2NH$—, —NHS$(O)_2$—, —C(O)—NH—, —NH—C(O)— or —$P(O)(CH_3)$—; and
      (B) unsubstituted or one, two or three times substituted with —OH, —$NH_2$, —C(O)OH, or —$P(O)(CH_3)_2$; or
    (4) once substituted with —C(O)OH and one, two or three times substituted with alkyl, which alkyl is:
      (A) optionally interrupted one, two or three times by —O—, —$S(O)_x$—, —$S(O)_2NH$—, —NHS$(O)_2$—, —C(O)—NH—, —NH—C(O)— or —$P(O)(CH_3)$—; and
      (B) unsubstituted or one, two or three times substituted with —OH, —$NH_2$, —C(O)OH, or —$P(O)(CH_3)_2$;

(b) pyrazolyl; which is:
  (1) unsubstituted; or
  (2) once substituted with —C(O)OH; or
  (3) one, two or three times substituted with alkyl, which alkyl is:
    (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
    (B) unsubstituted or one, two or three times substituted with —OH, —NH$_2$, —C(O)OH, or —P(O)(CH$_3$)$_2$; or
  (4) once substituted with —C(O)OH and one, two or three times substituted with alkyl, which alkyl is:
    (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
    (B) unsubstituted or one, two or three times substituted with —OH, —NH$_2$, —C(O)OH, or —P(O)(CH$_3$)$_2$;
(c) triazolyl; which is:
  (1) unsubstituted; or
  (2) once substituted with —C(O)OH; or
  (3) one, two or three times substituted with alkyl, which alkyl is:
    (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
    (B) unsubstituted or one, two or three times substituted with —OH, —NH$_2$, —C(O)OH, or —P(O)(CH$_3$)$_2$; or
  (4) once substituted with —C(O)OH and one, two or three times substituted with alkyl, which alkyl is:
    (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
    (B) unsubstituted or one, two or three times substituted with —OH, —NH$_2$, —C(O)OH, or —P(O)(CH$_3$)$_2$; and
(d) tetrazolyl, which is:
  (1) unsubstituted; or
  (2) once substituted with —C(O)OH; or
  (3) one, two or three times substituted with alkyl, which alkyl is:
    (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
    (B) unsubstituted or one, two or three times substituted with —OH, —NH$_2$, —C(O)OH, or —P(O)(CH$_3$)$_2$; or
  (4) once substituted with —C(O)OH and one, two or three times substituted with alkyl, which alkyl is:
    (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
    (B) unsubstituted or one, two or three times substituted with —OH, —NH$_2$, —C(O)OH, or —P(O)(CH$_3$)$_2$; and pharmaceutically acceptable salts or esters thereof.

In a more specific embodiment of the preceding preferred embodiment, B is an imidazolyl. In another specific embodiment of the preceding preferred embodiment B is a pyrazolyl. In a further specific embodiment of the preceding preferred embodiment B is a triazolyl. In yet another particular embodiment of the above preferred embodiment B is tetrazolyl.

Another preferred embodiment of the present invention are the compounds of formula I-A, wherein:

$R^2$ and $R^3$ are both hydrogen;

V and G are both —O—;

—W—X—Y— is —(CH$_2$)$_4$—;

B is selected from the group consisting of:
  (a) imidazolyl; which is:
    (1) unsubstituted; or
    (2) once substituted with 2-(2-hydroxyethoxy)ethyl, 1-hydroxyethyl, 2-hydroxyethyl, 2-(2-methoxyethoxy)-ethyl, hydroxymethyl, 2-methanesulfinyl-ethyl, 2-methanesulfonyl-ethyl, dimethylphosphinoylmethyl, methoxymethyl, carboxymethyl, 2-carboxyethyl, aminomethyl, 1-aminoethyl, or 2-aminoethyl;
  (b) triazolyl; which is:
    (1) unsubstituted; or
    (2) once substituted with 2-(2-hydroxyethoxy)ethyl, 1-hydroxyethyl, 2-hydroxyethyl, 2-(2-methoxyethoxy)-ethyl, hydroxymethyl, 2-methanesulfinyl-ethyl, 2-methanesulfonyl-ethyl, dimethylphosphinoylmethyl, methoxymethyl, carboxymethyl, 2-carboxyethyl, aminomethyl, 1-aminoethyl, or 2-aminoethyl;
  (c) tetrazolyl, which is:
    (1) unsubstituted; or
    (2) once substituted with 2-(2-hydroxyethoxy)ethyl, 1-hydroxyethyl, 2-hydroxyethyl, 2-(2-methoxyethoxy)-ethyl, hydroxymethyl, 2-methanesulfinyl-ethyl, 2-methanesulfonyl-ethyl, dimethylphosphinoylmethyl, methoxymethyl, carboxymethyl, 2-carboxyethyl, aminomethyl, 1-aminoethyl, or 2-aminoethyl; and pharmaceutically acceptable salts or esters thereof.

In a more specific embodiment of the preceding preferred embodiment, B is an imidazolyl. In another specific embodiment of the preceding preferred embodiment B is a triazolyl. In a further specific embodiment of the preceding preferred embodiment B is a tetrazolyl.

Such compounds are for example:

4-[4-(4-Imidazol-1-yl-butyl)-phenoxymethyl]-2-[2-(4-pentafluorosulfanyl-phenyl)-vinyl]-oxazole;

2-{1-[4-(4-{2-[(E)-2-(-4-Pentafluorosulfanyl-phenyl)-vinyl]-oxazol-4-ylmethoxy}-phenyl)-butyl]-1H-imidazol-2-yl}-ethanol;

1-[4-(4-{2-[(E)-2-(-4-Pentafluorosulfanyl-phenyl)-vinyl]-oxazol-4-ylmethoxy}-phenyl)-butyl]-1H-[1,2,3]triazole;

4-[4-(4-{2-[(E)-2-(-4-Pentafluorosulfanyl-phenyl)-vinyl]-oxazol-4-ylmethoxy}-phenyl)-butyl]-1H-[1,2,3]triazole;

5-[4-(4-{2-[(E)-2-(-4-Pentafluorosulfanyl-phenyl)-vinyl]-oxazol-4-ylmethoxy}-phenyl)-butyl]-2H-tetrazole;

2-{5-[4-(4-{2-[2-(4-Pentafluorosulfanyl-phenyl)-vinyl]-oxazol-4-ylmethoxy}-phenyl)-butyl]-tetrazol-1-yl}-ethanol; and 2-{5-[4-(4-{2-[2-(4-Pentafluorosulfanyl-phenyl)-vinyl]-oxazol-4-ylmethoxy}-phenyl)-butyl]-tetrazol-2-yl}-ethanol.

Another preferred embodiment of the present invention are the compounds of formula I-A, wherein:

$R^2$ and $R^3$ are both hydrogen;

V and G are both —O—;

—W—X—Y— is —O—(CH$_2$)$_3$—, —C(O)—(CH$_2$)$_3$—, —S—(CH$_2$)$_3$—, —S(O)$_2$—(CH$_2$)$_3$—, —S(O)—(CH$_2$)$_3$—, —S(O)$_2$—NH—(CH$_2$)$_2$—, —NH—C(O)—(CH$_2$)$_2$—, —C(O)—NH—(CH$_2$)$_2$—, —CH$_2$—NH—(CH$_2$)$_2$—, —CH$_2$—O—(CH$_2$)$_2$—, —CH$_2$—S(O)—(CH$_2$)$_2$—, —CH$_2$—S(O)$_2$—(CH$_2$)$_2$—, —CH=CH—CH$_2$—, —CH=CH—(CH$_2$)$_2$—, —CH$_2$—CH=CH—CH$_2$—, or —C≡C—(CH$_2$)$_2$—;

B is selected from the group consisting of:
  (a) imidazolyl; which is:
    (1) unsubstituted; or
    (2) once substituted with —C(O)OH; or
    (3) one, two or three times substituted with alkyl, which alkyl is:
      (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
      (B) unsubstituted or one, two or three times substituted with —OH, —NH$_2$, —C(O)OH, or —P(O)(CH$_3$)$_2$; or
    (4) once substituted with —C(O)OH and one, two or three times substituted with alkyl, which alkyl is:
      (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
      (B) unsubstituted or one, two or three times substituted with —OH, —NH$_2$, —C(O)OH, or —P(O)(CH$_3$)$_2$;
  (b) pyrazolyl; which is:
    (1) unsubstituted; or
    (2) once substituted with —C(O)OH; or
    (3) one, two or three times substituted with alkyl, which alkyl is:
      (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
      (B) unsubstituted or one, two or three times substituted with —OH, —NH$_2$, —C(O)OH, or —P(O)(CH$_3$)$_2$; or
    (4) once substituted with —C(O)OH and one, two or three times substituted with alkyl, which alkyl is:
      (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
      (B) unsubstituted or one, two or three times substituted with —OH, —NH$_2$, —C(O)OH, or —P(O)(CH$_3$)$_2$;
  (c) triazolyl; which is:
    (1) unsubstituted; or
    (2) once substituted with —C(O)OH; or
    (3) one, two or three times substituted with alkyl, which alkyl is:
      (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
      (B) unsubstituted or one, two or three times substituted with —OH, —NH$_2$, —C(O)OH, or —P(O)(CH$_3$)$_2$; or
    (4) once substituted with —C(O)OH and one, two or three times substituted with alkyl, which alkyl is:
      (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
      (B) unsubstituted or one, two or three times substituted with —OH, —NH$_2$, —C(O)OH, or —P(O)(CH$_3$)$_2$; and
  (d) tetrazolyl, which is:
    (1) unsubstituted; or
    (2) once substituted with —C(O)OH; or
    (3) one, two or three times substituted with alkyl, which alkyl is:
      (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
      (B) unsubstituted or one, two or three times substituted with —OH, —NH$_2$, —C(O)OH, or —P(O)(CH$_3$)$_2$; or
    (4) once substituted with —C(O)OH and one, two or three times substituted with alkyl, which alkyl is:
      (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
      (B) unsubstituted or one, two or three times substituted with —OH, —NH$_2$, —C(O)OH, or —P(O)(CH$_3$)$_2$; and pharmaceutically acceptable salts or esters thereof.

In a more specific embodiment of the preceding preferred embodiment, B is an imidazolyl. In another specific embodiment of the preceding preferred embodiment B is a pyrazolyl. In a further specific embodiment of the preceding preferred embodiment B is a triazolyl. In yet another particular embodiment of the foregoing preferred embodiment B is tetrazolyl.

Still a preferred embodiment of the present invention are the compounds of formula I-A, wherein:

$R^2$ and $R^3$ are both hydrogen;

V and G are both —O—;

—W—X—Y— is —O—(CH$_2$)$_3$—, —S(O)$_2$—NH—(CH$_2$)$_2$—, —CH$_2$—O—(CH$_2$)$_2$—, —CH$_2$—S(O)—(CH$_2$)$_2$—, —CH$_2$—S(O)$_2$—(CH$_2$)$_2$—, —CH=CH—(CH$_2$)$_2$—, or —C≡C—(CH$_2$)$_2$—;

B is triazolyl; and pharmaceutically acceptable salts or esters thereof.

Such compounds are for example:

1-[2-(4-{2-[-4-(Pentafluorosulfanyl-phenyl)-vinyl]-oxazol-4-ylmethoxy}-benzyloxy)-ethyl]-1H-[1,2,3]-triazole;

1-[2-(4-{2-[(E)-2-(4-Pentafluorosulfanyl-phenyl)-vinyl]-oxazol-4-ylmethoxy}-phenylmethanesulfinyl)-ethyl]-1H-[1,2,3]triazole;

1-[2-(4-{2-[(E)-2-(4-Pentafluorosulfanyl-phenyl)-vinyl]-oxazol-4-ylmethoxy}-phenylmethanesulfonyl)-ethyl]-1H-[1,2,3 ]triazole;

1-[4-(4-{2-[2-(4-Pentafluorosulfanyl-phenyl)-vinyl]-oxazol-4-ylmethoxy}-phenyl)-but-3-enyl]-1H-[1,2,3]triazole;

1-[4-(4-{2-[2-(4-Pentafluorosulfanyl-phenyl)-vinyl]-oxazol-4-ylmethoxy}-phenyl)-but-3-ynyl]-1H-[1,2,3]triazole;

N-(2-[1,2,3]Triazol-1-yl-ethyl)-4-{2-[2-(4-pentafluorosulfanyl-phenyl)-vinyl]-oxazol-4-ylmethoxy}-benzenesulfonamide; and 1-[3-(4-{2-[2-(4-Pentafluorosulfanyl-phenyl)-vinyl]-oxazol-4-ylmethoxy}-phenoxy)-propyl]-1H-[1,2,3]triazole.

Still a preferred embodiment of the present invention are the compounds of formula I-A, wherein:

$R^2$ and $R^3$ are both hydrogen;

G is —O— or —S—;

V is —NH—, —C(O)—NH—, —NH—C(O)— or —S(O)$_x$—;

—W—X—Y— is —(CH$_2$)$_4$—;

B is selected from the group consisting of:
(a) imidazolyl; which is:
  (1) unsubstituted; or
  (2) once substituted with —C(O)OH; or
  (3) one, two or three times substituted with alkyl, which alkyl is:
    (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
    (B) unsubstituted or one, two or three times substituted with —OH, —NH$_2$, —C(O)OH, or —P(O)(CH$_3$)$_2$; or
  (4) once substituted with —C(O)OH and one, two or three times substituted with alkyl, which alkyl is:
    (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
    (B) unsubstituted or one, two or three times substituted with —OH, —NH$_2$, —C(O)OH, or —P(O)(CH$_3$)$_2$;
(b) pyrazolyl; which is:
  (1) unsubstituted; or
  (2) once substituted with —C(O)OH; or
  (3) one, two or three times substituted with alkyl, which alkyl is:
    (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
    (B) unsubstituted or one, two or three times substituted with —OH, —NH$_2$, —C(O)OH, or —P(O)(CH$_3$)$_2$; or
  (4) once substituted with —C(O)OH and one, two or three times substituted with alkyl, which alkyl is:
    (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
    (B) unsubstituted or one, two or three times substituted with —OH, —NH$_2$, —C(O)OH, or —P(O)(CH$_3$)$_2$;
(c) triazolyl; which is:
  (1) unsubstituted; or
  (2) once substituted with —C(O)OH; or
  (3) one, two or three times substituted with alkyl, which alkyl is:
    (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
    (B) unsubstituted or one, two or three times substituted with —OH, —NH$_2$, —C(O)OH, or —P(O)(CH$_3$)$_2$; or
  (4) once substituted with —C(O)OH and one, two or three times substituted with alkyl, which alkyl is:
    (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
    (B) unsubstituted or one, two or three times substituted with —OH, —NH$_2$, —C(O)OH, or —P(O)(CH$_3$)$_2$; and
(d) tetrazolyl, which is:
  (1) unsubstituted; or
  (2) once substituted with —C(O)OH; or
  (3) one, two or three times substituted with alkyl, which alkyl is:
    (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
    (B) unsubstituted or one, two or three times substituted with —OH, —NH$_2$, —C(O)OH, or —P(O)(CH$_3$)$_2$; or
  (4) once substituted with —C(O)OH and one, two or three times substituted with alkyl, which alkyl is:
    (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
    (B) unsubstituted or one, two or three times substituted with —OH, —NH$_2$, —C(O)OH, or —P(O)(CH$_3$)$_2$;

x is 0, 1 or 2; and pharmaceutically acceptable salts or esters thereof.

In a more specific embodiment of the preceding preferred embodiment, B is an imidazolyl. In another specific embodiment of the preceding preferred embodiment B is a pyrazolyl. In a further specific embodiment of the preceding preferred embodiment B is a triazolyl. In yet another particular embodiment of the foregoing preferred embodiment B is tetrazolyl.

Still a preferred embodiment of the present invention are the compounds of formula I-A, wherein:

$R^2$ and $R^3$ are both hydrogen;

G is —O— or —S—

V is —NH—, —C(O)—NH—, —NH—C(O)—, or —S(O)$_x$—;

—W—X—Y— is —O—(CH$_2$)$_3$—, —C(O)—(CH$_2$)$_3$—, —S—(CH$_2$)$_3$—, —S(O)$_2$—(CH$_2$)$_3$—, —S(O)—(CH$_2$)$_3$—, —S(O)$_2$—NH—(CH$_2$)$_2$—, —NH—C(O)—(CH$_2$)$_2$—, —C(O)—NH—(CH$_2$)$_2$—, —CH$_2$—NH—(CH$_2$)$_2$—, —CH$_2$—O—(CH$_2$)$_2$—, —CH$_2$—S(O)—(CH$_2$)$_2$—, —CH$_2$—S(O)$_2$—(CH$_2$)$_2$—, —CH=CH—CH$_2$—, —CH=CH—(CH$_2$)$_2$—, —CH$_2$—CH=CH—CH$_2$—, or —C≡C—(CH$_2$)$_2$—;

B is selected from the group consisting of:
(a) imidazolyl; which is:
  (1) unsubstituted; or
  (2) once substituted with —C(O)OH; or
  (3) one, two or three times substituted with alkyl, which alkyl is:

(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$; or
(4) once substituted with —C(O)OH and one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$;
(b) pyrazolyl; which is:
(1) unsubstituted; or
(2) once substituted with —C(O)OH; or
(3) one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$; or
(4) once substituted with —C(O)OH and one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$;
(c) triazolyl; which is:
(1) unsubstituted; or
(2) once substituted with —C(O)OH; or
(3) one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$; or
(4) once substituted with —C(O)OH and one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$; and
(d) tetrazolyl, which is:
(1) unsubstituted; or
(2) once substituted with —C(O)OH; or
(3) one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$; or
(4) once substituted with —C(O)OH and one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$;
x is 0, 1 or 2; and pharmaceutically acceptable salts or esters thereof.

In a more specific embodiment of the preceding preferred embodiment, B is an imidazolyl. In another specific embodiment of the preceding preferred embodiment B is a pyrazolyl. In a further specific embodiment of the preceding preferred embodiment B is a triazolyl. In yet another particular embodiment of the foregoing preferred embodiment B is tetrazolyl.

Still a preferred embodiment of the present invention are the compounds of formula I-A, wherein:
$R^2$ and $R^3$ are both hydrogen;
G is —O—;
V is —NH— or —S(O)$_2$—;
—W—X—Y— is —O—(CH$_2$)$_3$—, —S(O)$_2$—NH—(CH$_2$)$_2$—, —CH$_2$—O—(CH$_2$)$_2$—, —CH$_2$—S(O)—(CH$_2$)$_2$—, —CH$_2$—S(O)$_2$—(CH$_2$)$_2$—, —CH=CH—(CH$_2$)$_2$—, or —C≡C—(CH$_2$)$_2$—;
B is triazolyl; and pharmaceutically acceptable salts or esters thereof.

Such a compound is for example:
[4-(4-[1,2,3]Triazol-1-yl-but—1-enyl)-phenyl]-{2-[2-(4-pentafluorosulfanyl-phenyl)-vinyl]-oxazol-4-ylmethyl}-amine.

Still a preferred embodiment of the present invention are the compounds of formula I-A, wherein:
$R^2$ and $R^3$ are both hydrogen;
G is —O—;
V is —NH— or —S(O)$_2$—;
—W—X—Y— is —(CH$_2$)$_4$—;
B is triazolyl; and pharmaceutically acceptable salts or esters thereof.

Such compounds are for example:
[4-(4-[1,2,3]Triazol-1-yl-butyl)-phenyl]-{2-[2-(4-pentafluorosulfanyl-phenyl)-vinyl-oxazol-4-ylmethyl}-amine; and
1-[4-(4-{2-[2-(4-Pentafluoromethanesulfanyl-phenyl)-vinyl]-oxazol-4-ylmethanesulfonyl}-phenyl)-butyl]-1H-[1,2,3]triazole.

Still another embodiment of the present invention is a process for the manufacture of the compounds of formula I-A, wherein:

a) a compound of formula II-A

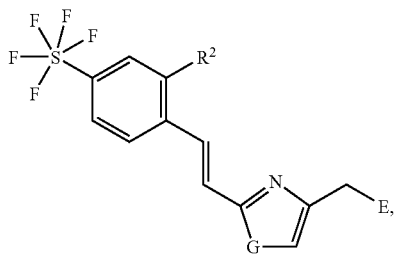
(formula II-A)

wherein $R^2$ and G have the meaning given for formula I-A and E denotes a suitable leaving group, is reacted with a compound of formula III-A

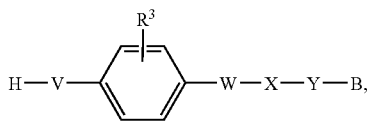
(formula III-A)

wherein $R^3$, V, W, X, Y and B have the meaning given for formula I-A;

b) a protecting group, if present to protect the heteroatoms in the imidazole-, pyrazole-, triazole- or tetrazole ring of "B" from undesired side reactions is cleaved to give a compound of formula I-A;

c) said compound of formula I-A is isolated from the reaction mixture; and d) if desired is turned into a pharmaceutically acceptable salt.

The compounds of the general formula I-A, or a pharmaceutically acceptable salt or ester thereof, may be prepared by any process known to be applicable for the preparation of chemically-related compounds by the one skilled in the art. Such processes, when used to prepare the compounds of formula I-A, or a pharmaceutically-acceptable salt or ester thereof, are provided as a further feature of the invention. Necessary starting materials may be obtained by standard procedures of organic chemistry. The preparation of such starting materials is described within the accompanying non-limiting examples. Alternatively necessary starting materials are obtainable by analogous procedures to those illustrated which are within the ordinary skill of an organic chemist.

In detail, the preparation of the compounds according to the present invention may vary according to the nature of the group —W—X—Y—. Therefore, further embodiments of the present invention are the processes for the manufacture of the compounds of formula I-A as described below.

In one embodiment, if W in formula I-A denotes —$CH_2$— and X is —NH— or —O— or —$S(O)_x$—, the corresponding compounds according to the present invention may also be prepared by reacting a compound of formula IV-A

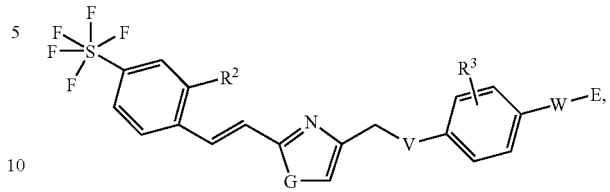
(formula IV-A)

wherein $R^2$, $R^3$, G, V and W have the meanings given for formula I-A, and E denotes a suitable leaving group as defined below, preferably iodide, bromide or chloride, p-toluenesulfonate (tosylate), methanesulfonate (mesylate), trifluoromethansulfonate (triflate) or the azido group, with a compound of formula V-A X'—Y—B     (formula V-A), wherein Y and B have the meanings given for formula I-A, and X' denotes —$NH_2$, —OH or —$S(O)_xH$, wherein x is 0,1 or 2.

In another embodiment, if W in formula I-A denotes —$CH_2$— and X is —NH—, the corresponding compounds of the present invention may also be prepared by reacting a compound of formula VI-A

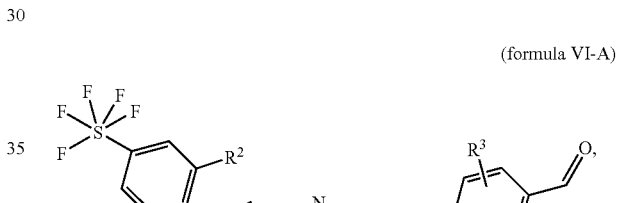
(formula VI-A)

wherein $R^2$, $R^3$, G and V have the meanings given for formula I-A, with a compound of formula VII-A X"—Y—B     (formula VII-A), wherein Y and B have the meanings given before and X" denotes —$NH_2$, under conditions of a reductive amination.

In still another embodiment, if W and X in formula I-A denote —$CH_2$—, the corresponding compounds according to the present invention may also be prepared by reacting a compound of formula VIII-A

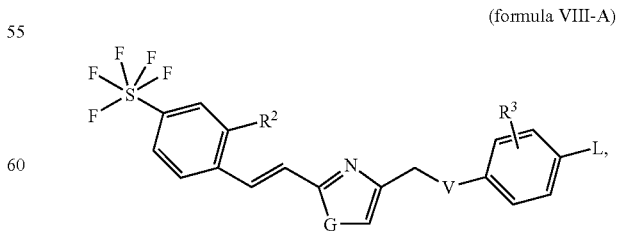
(formula VIII-A)

wherein $R^2$, $R^3$, G and V have the meanings given for formula I-A, and L denotes halogen or triflate, with a compound of formula IX-A

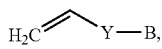

(formula IX-A)

wherein Y and B have the meanings given herein before, and whereby said compound of formula IX-A, prior to its reaction with said compound of formula VIII-A is hydroborated using 9-borobicyclo[3.3.1]nonane and a palladium catalyst, preferably [1,1'-Bis(diphenyl-phosphino)-ferrocene]dichloropalladium(II).

The reaction of a compound of formula II-A with a compound of formula III-A, or of a compound of formula IV-A with a compound of formula V-A is an alkylation reaction, which is well known to the skilled artisan. Typically, the alkylation may be carried out in solvents like N,N-dimethylformamide (DMF), methanol, ethanol and isopropanol. Typical bases for this reaction are alkaline carbonates, sodium methylate, sodium hydride or lithium diisopropyl amide. The reaction temperatures may vary from 20° C. to 150° C. Preferred alkylation procedures make use of alkaline carbonates as bases in solvents like ketones, for example cesium carbonate in butanone at reflux temperature, or sodium hydride in DMF at room temperature. Suitable leaving groups "E" are those typically used in alkylation reactions and well known to the skilled artisan. Examples of such leaving groups are, among others, the anions of halogens, especially iodide, bromide or chloride, p-toluenesulfonate (tosylate), methanesulfonate (mesylate), trifluoromethansulfonate (triflate) or the azido group.

Reaction of a compound of formula VI-A with a compound of formula VII-A under conditions of reductive amination is typically achieved in solvents like acetonitrile, N,N-dimethylformamide, methanol or ethanol and at temperatures between 20° C. and 150° C. Reducing agents typically employed are e.g. sodium cyanoborohydride (NaCNBH$_3$), sodium borohydride (NaBH$_4$) or lithium aluminium hydride (LiAlH$_4$).

Reaction of a compound of formula VIII-A with a compound of formula IX-A is typically achieved in solvents like tetrahydrofuran (THF), N,N-dimethylformamide, acetone or mixtures thereof and at temperatures between 0° C. and 150° C. In a first step, the olefin of formula IX-A is hydroborated, for example with 9-borobicyclo[3.3.1]nonane (9-BBN). Then the resulting boron derivative is coupled to the compound of formula VIII-A using palladium catalysts, for example [1,1'-Bis(diphenylphosphino)ferrocene]-dichloropalladium(II) (PdCl$_2$(dppf)), in the presence of a base like aqueous cesium carbonate or aqueous sodium carbonate or sodium ethylate.

The reactions described above may require protection of heteroatoms, such as nitrogen in the imidazole, pyrazole, triazole or tetrazole rings of group "B" from undesired side reactions. Therefore, subsequent to any reaction procedure described above, a protecting group if present to protect a hetero atom in an imidazole, pyrazole, triazole or tetrazole group of "B" is removed. Removal of a protecting group on a hetero atom in group "B" depends on the nature of such group. However, the use of protection groups in order to protect heteroatoms within an imidazole, pyrazole, triazole or tetrazole of the group "B" from undesired reactions, is within the ordinary skill of an organic chemist. Typical examples are the removal of a trityl group under acidic conditions, for example with aqueous formic acid in THF under reflux or the removal of a substituted silyl group with tetrabutylammonium fluoride in aqueous THF at room temperature.

The compounds of formula I-A and their pharmaceutically acceptable salts or esters possess valuable pharmacological properties. It has been found that said compounds inhibit the HER-signaling pathway and show anti-proliferative activity. Consequently the compounds of the present invention are useful in the therapy and/or prevention of illnesses with known over-expression of receptor tyrosine kinases of the HER-family like HER-2 and EGFR (HER-1), especially in the therapy and/or prevention of illnesses mentioned above. The activity of the present compounds as HER-signaling pathway inhibitors is demonstrated by the following biological assays:

Inhibition of HER2 Phosphorylation in Calu3 Tumor Cell Line $2 \times 10^5$ Calu3 cells per well were plated in a 12-well plate. After 4 days cells were starved for 16 h in DMEM (Dulbecco's Modified Eagle Medium)/0.5% FCS/1% glutamine. During this time cells were incubated with 1M of a compound according to this invention. Afterwards cells were lysed in lyses buffer containing 1% Triton, 10% glycerol, 1 mM EGTA, 1.5 mM MgCl$_2$, 150 mM NaCl, 50 mM Hepes pH 7.5, 1 mM PMSF, 10 µg/mL aprotinin and 0.4 mm orthovanadate. Cell lysates were analyzed on a SDS PAGE and after transfer to a nitrocellulose membrane detected with a rabbit antibody specifically recognizing the pY 1248 in HER2 (Cell Signaling). After incubation with an anti rabbit antibody coupled to POD (Peroxidase from Biorad, Munich, Germany) signals were detected by chemiluminescence (ECL, Amersham). Inhibition of HER2 phosphorylation is calculated as percentage of the DMSO treated control. This percentage is calculated according to the following formula:
Inhibition in %=100−(Phosphorylated-HER2-Signal of Test Sample*100/Phosphorylated-HER2-Signal DMSO-control).

With all compounds a significant inhibition of HER2-phosphorylation was detected, with compounds from examples 1, 4, 9, 11, 12, 14, 15 and 16 showing a higher percentage of inhibition of phosphorylation than with 1-[4-(4-{2-[2-(4-Trifluoromethyl-phenyl)-vinyl]-oxazol-4-yl-methoxy}-phenyl)-butyl]-1H-[1,2,3]-triazole (Example 4, p. 88, WO 01/77107) as reference compound.

TABLE 1

| | Control (DMSO) | Percent inhibition of HER2-phosphorylation (compound concentration 1 µM) |
|---|---|---|
| reference compound | 0 | 52.3 |
| example 1 | 0 | 87.5 |
| example 4 | 0 | 86.1 |
| example 9 | 0 | 52.9 |
| example 11 | 0 | 59.7 |
| example 12 | 0 | 68.8 |
| example 14 | 0 | 71.7 |
| example 15 | 0 | 97.5 |
| example 16 | 0 | 91.9 |

In Vivo Assay on Tumor Inhibition:

To generate primary tumors, NSCLC (e.g. QG56, A549, Calu-3) cells (4–5.0×10$^6$ in a volume of 100µl) are injected subcutaneously into the left flank of female SCID beige mice (Severe Combined Immunodeficient/beige mice available from Charles River, Sulzfeld, Deutschland) or BALB/c nude mice (BALB/c Nude Spontaneous Mutant Mice [homozygotes] available from Taconic Europe [former M&B A/S (Mollegaard and Bomholtgard Breeding and Research Centre) in Denmark]) using a 1 ml syringe and a 26 G needle. The tumor cells are originally obtained from the NCI and deposited in a working cell bank. The cells are thawed and expanded in vitro before use in the experiment. Mice are assigned to the treatment groups 14–21 days after cell injection. For grouping (n=10–15 mice per group), the animals are randomized to get a similar mean primary tumor volume of ca. 100–150 mm³ per group. The test compounds are administered orally once per day as a suspension in 7.5% gelatine 0.22% NaCl with an administration volume of 10 ml/kg based on actual body weights. Treatment is initiated one day after staging, and carried out until day 20–50, the final day of the study. The subcutaneous primary tumors are measured twice weekly, starting prior to randomisation, in two dimensions (length and width) using an electronic caliper. The volume of the primary tumor is calculated using the formula: $V[mm^3]=(length\ [mm] \times width\ [mm] \times width\ [mm])/2$. In addition, the body weight of all animals is recorded at least twice weekly. Finally, at the end of the study the tumors are explanted and weighed.

The compounds according to this invention and their pharmaceutically acceptable salts or esters can be used as medicaments, e.g. in the form of pharmaceutical composition. The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically inert, inorganic or organic carriers. As used herein, a "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions. For example, lactose, corn starch or derivatives thereof, talc, stearic acids or its salts and the like can be used, as such carriers for tablets, coated tablets, dragees and hard gelatine capsules. Suitable carriers for soft gelatine capsules are, for example, vegetable oils, waxes, fats, semi-solid and liquid polyols and the like. However, depending on the nature of the active substance, carriers may not be required for some soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Preferred pharmaceutical compositions comprise the following:

a) Tablet Formulation (Wet Granulation):

| Item | Ingredients | Mg/tablet | | | |
|---|---|---|---|---|---|
| 1. | Compound of formula(I-A) | 5 | 25 | 100 | 500 |
| 2. | Lactose Anhydrous DTG | 125 | 105 | 30 | 150 |
| 3. | Sta-Rx 1500 (a pre-gelatinized starch powder) | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

b) Capsule Formulation:

| Item | Ingredients | mg/capsule | | | |
|---|---|---|---|---|---|
| 1. | Compound of formula (I-A) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

c) Micro Suspension
1. Weigh 4.0 g glass beads in custom made tube GL 25, 4 cm (the beads fill half of the tube).
2. Add 50 mg compound, disperse with spatulum and vortex.
3. Add 2 ml gelatin solution (weight beads: gelatin solution=2:1) and vortex.
4. Cap and wrap in aluminium foil for light protection.
5. Prepare a counter balance for the mill.
6. Mill for 4 hours, 20/s in a Retsch mill (for some substances up to 24 hours at 30/s).
7. Extract suspension from beads with two layers of filter (100 μm) on a filter holder, coupled to a recipient vial by centrifugation at 400 g for 2 min.
8. Move extract to measuring cylinder.
9. Repeat washing with small volumes (here 1 ml steps) until final volume is reached or extract is clear.
10. Fill up to final volume with gelatin and homogenize.

The above described preparation yields micro-suspensions of the compounds of formula I-A with particle sizes between 1 and 10 μm. The suspensions are suitable for oral applications and can be used in the in vivo assay described above.

Pharmaceutical compositions containing a compound of formula I-A or a pharmaceutically acceptable salt or ester thereof and a therapeutically inert carrier are also an object of the present invention, as is a process for their production, which comprises bringing one or more compounds of formula I-A and/or pharmaceutically acceptable salts or esters and, if desired, one or more other therapeutically valuable substances into a galenical administration form together with one or more therapeutically inert carriers.

In accordance with the invention compounds of formula I-A as well as their pharmaceutically acceptable salts or esters are useful in the control or prevention of illnesses. Based on their HER-signaling pathway inhibition and their antiproliferative activity, said compounds are useful for the treatment of diseases such as cancer in humans or animals and for the production of corresponding pharmaceutical compositions. The dosage depends on various factors such as manner of administration, species, age and/or individual state of health.

Consequently, the present invention also provides the following preferred embodiments:
(1) a process for the manufacture of the compounds of formula I-A or a salt or ester thereof
(2) a pharmaceutical composition, containing one or more compounds of formula I-A, together with pharmaceutically acceptable excipients;
(3) a pharmaceutical composition as defined above for the inhibition of tumor growth;
(4) the use of one or more compounds of formula I-A for the treatment of cancer;
(5) the use of one or more compounds of formula I-A for the manufacture of pharmaceutical compositions;
(6) the use of one or more compounds of formula I-A for the manufacture of corresponding pharmaceutical compositions for the inhibition of tumor growth.

The following examples and references are provided to aid the understanding of the present invention, the true scope of which is set forth in the appended claims. It is understood that modifications can be made in the procedures set forth without departing from the spirit of the invention.

EXAMPLE 1

4-[4-(4-Imidazol-1-yl-butyl)-phenoxymethyl]-2-[2-(4-pentafluorosulfanyl-phenyl)-vinyl]-oxazole i) 1-(4-Bromo-butyl)-4-methoxy-benzene After starting the Grignard reaction by adding 5.00 ml 4-bromoanisole to a mixture of 4.86 g (0.20 mol) magnesium turnings and 100 ml THF, 20.00 ml 4-bromoanisole (total: 25.0 ml 37.4 g; 0.20 mol) were added at a pace sufficient to maintain reflux temperature. The reaction mixture was heated to reflux for additional 3 h, cooled to r.t. and dropped at 0° C. within 1 h to a stirred solution prepared by mixing 129.6 g (71.6 ml, 0.60 mol) 1,4-dibromo-butane in 200 ml THF with a freshly prepared solution of 0.17 g (4.0 mmol) LiCl and 0.267 g (2.0 mmol) Cu(II)Cl$_2$ in 20 ml THF. Stirring was continued for 12 h at r.t. followed by the addition of 100 ml of a 20% ammonium chloride solution and 200 ml ethyl acetate. The water phase was extracted twice with 50 ml ethyl acetate, all organic phases were combined, dried over sodium sulphate and evaporated. The resulting oil was fractionated by vacuum distillation. Yield: 27.7 g (57%), b.p. 112–115° C./0.15 mbar.

ii) 1-[4-(4-Methoxy-phenyl)-butyl]-1H-imidazole

A mixture of 3.65 g (15.0 mmol) 1-(4-bromo-butyl)-4-methoxy-benzene, 1.02 g (15.0 mmol) imidazole, 2.74 g (16.5 mmol) potassium iodide, 0.60 g (15.0 mmol) sodium hydroxide and 20 ml 2-methyl-2-butanol was heated to reflux for 7 h. Solvents were distilled off, the residue dissolved in ethyl acetate and washed with water. Drying over Na$_2$SO$_4$ and removal of solvents in vacuo gave 2.0 g (58%) slightly colored oil.

MS: M=231.2 (ESI+)

$^1$H-NMR(400 MHz, D$_6$-DMSO): δ=1.45 (quintet, 2H, CH$_2$—CH$_2$—Ar), 1.68 (quintet, 2H, CH$_2$—CH$_2$-imidazole), 2.51 (t, 2H, CH$_2$—Ar), 3.71 (s, 3H, OCH$_3$), 3.96 (t, 2H, CH$_2$-imidazole), 6.83 (d, 2H, 3'-/5'-H), 6.86 (s, 1H, imidazole), 7.07 (d, 2H, 2'-/6'-H), 7.13 (s, 1H, imidazole), 7.59 (s, 1H, 2-H, imidazole).

iii) 4-(4-Imidazol-1-yl-butyl)-phenol 1.90 g (8.25 mmol) 1-[4-(4-methoxy-phenyl)-butyl]-1H-imidazole and 28 ml (247 mmol) 48% aqueous hydrobromic acid were stirred at 80° C. for 10 h. The mixture was cooled to 0° C., 23 ml of 4 N NaOH added, extracted with toluene and the aqueous phase adjusted to pH=6.3 by addition of 6 N HCl. The resulting precipitate was isolated, washed with ethyl acetate/n-heptane 2:1 and dried. 1.2 g (67%) slightly yellow powder.

MS: M=217.2 (ESI+)

$^1$H-NMR(400 MHz, D$_6$-DMSO): δ=1.42 (quintet, 2H, CH$_2$—CH$_2$—Ar), 1.68 (quintet, 2H, CH$_2$—CH$_2$-imidazole), 2.50 (t, 2H, CH$_2$—Ar), 3.96 (t, 2H, CH$_2$-imidazole), 6.65 (d, 2H, 2'-/6'-H), 6.90 (s, 1H, imidazole), 6.94 (d, 2H, 3'-/5'-H), 7.16 (s, 1H, imidazole), 7.66 (s, 1H, 2-H, imidazole), 9.12 (br, 1H, OH).

iv) 3-(4-Pentafluorosulfanyl-phenyl)-acrylic acid

A mixture of 5.40 g (23.3 mmol) 4-pentafluorosulfanyl-benzaldehyde, 2.42 g (23.3 mmol) malonic acid, 0.20 g (2.3 mmol) piperidine and 10.0 ml pyridine was kept at reflux temperature until carbon dioxide development ceased (4 h). The reaction mixture was poured into a solution of 100 ml ice and 60 ml 6N HCl. The precipitate was isolated, washed with water, then with n-heptane and dried in vacuum at 40° C. Yield: 5.73 g (90%) 3-(4-pentafluorosulfanyl-phenyl)-acrylic acid.

MS: M=273.2 (ESI−)

$^1$H-NMR(400 MHz, D$_6$-DMSO): δ=6.69 (d, J=15.8 Hz, 1H, 2-H), 7.65 (d, J=15.8 Hz, 1H, 3-H), 7.92 (s, 4H, Ar—SF$_5$), 12.7 (br, 1H, COOH).

$^{19}$F-NMR(376 MHz, D$_6$-DMSO): δ=63.5 (d, 4F), 86.3 (quintet, 1F).

v) 3-(4-Pentafluorosulfanyl-phenyl)-acrylamide

To a suspension of 5.70 g (20.8 mmol) 3-(4-pentafluorosulfanyl-phenyl)-acrylic acid in 30 ml tetrahydrofuran and 0.21 ml N,N-dimethyl formamide a solution of 3.47 ml (27.4 mmol) oxalyl chloride in 5.0 ml tetrahydrofuran was added dropwise at 0° C. within 10 min. Stirring was continued at 0–5° C. for 30 min. and 3 h at room temperature thereafter. The resulting solution was cooled to 0–5° C. again and then added within 15 min. to mixture of 300 ml ice and 120 ml of a 25% aqueous ammonia solution. The precipitated amide was collected, washed with water and n-heptane and dried at 40° C. in vacuo. Yield 5.17 g (91%) 3-(4-pentafluorosulfanyl-phenyl)-acrylamide.

MS: M=274.2(ESI+), 272.2(ESI−)

¹H-NMR(400 MHz, D₆-DMSO): δ=6.76 (d, J=15.8 Hz, 1H, 2-H), 7.26 (s, br, 1H, NH), 7.48 (d, J=15.8 Hz, 1H, 3-H), 7.66 (br, 1H, NH), 7.78 (d, 2H, Ar—SF₅), 7.93 (d, 2H, ArSF₅).

¹⁹F-NMR(376 MHz, D₆-DMSO): δ=63.7 (d, 4F), 86.8 (quintet, 1F).

vi) 4-Chloromethyl-2-[2-(4-pentafluorosulfanyl-phenyl)-vinyl]-oxazole 4.10 g (15.0 mmol) 3-(4-pentafluorosulfanyl-phenyl)-acrylamide, 2.37 g (18.7 mmol) dichloro acetone and 25.0 ml toluene were kept at reflux temperature for 12 h with continuous removal of water by use of a Dean-Stark trap (a water separator used in chemical reactions). The reaction mixture was evaporated and purified by chromatography on silica gel (eluent:heptane/ethyl acetate 5:1). All fractions containing the product were evaporated and the residue stirred with 10 ml isohexane, the crystallized material isolated by filtration dried. 4.40 g (85%) 4-Chloromethyl-2-[2-(4-pentafluoromsulfanyl-phenyl)-vinyl]-oxazole.

MS: M=346.1(APCI+), 344.2(APCI−).

¹H-NMR(400 MHz, D₆-DMSO): δ=4.72 (s, 2H, CH₂Cl), 7.35 (d, 1H, =CH), 7.62 (d, 1H, =CH), 7.94 (m, 4H, Ar—H), 8.23 (s, 1H, oxazole).

vii) 4-[4-(4-Imidazol-1-yl-butyl)-phenoxymethyl]-2-[2-(4-pentafluorosulfanyl-phenyl)-vinyl]-oxazole 25.0 mg (0.100 mmol) 95% sodium hydride were given to a solution of 216 mg (0.100 mmol) 4-(4-[Imidazol-1-yl]-butyl)-phenol in 5.0 ml DMF and stirred for 15 min. 346 mg (0.100 mmol) 4-chloromethyl-2-[2-(4-pentafluorosulfanyl-phenyl)-vinyl]-oxazole were added and stirring continued overnight. After addition of 10 ml water the resulting precipitate was isolated and washed with 2×10 ml water, 2×10 ml methanol and with diethyl ether. Yield 411 mg (78%). MS: M=526.2 (ESI+)

¹H-NMR (400 MHz, CDCl₃): δ=1.45 (quintet, 2H, CH₂—CH₂—Ar), 1.69 (quintet, 2H, CH₂—CH₂-imidazole), 2.52 (t, 2H, CH₂—Ar), 3.96 (t, 2H, CH₂-imidazole), 4.99 (s, 2H, OCH₂), 6.87 (s, 1H, imidazole), 6.94 (d, 2H, 2'-/6'-H—Ar), 7.09 (d, 2H; 2H, 3'-/5'-H—Ar); 7.14 (s, 1H, imidazole), 7.35 (d, 1H, vinyl-H), 7.60 (s, 1H, 2-H, imidazole), 7.61 (d, 1H, vinyl-H), 7.70 (s, 1H, oxazole), 7.94 (m, 4H, ArSOCF₃), 8.25 (s, 1H, oxazole).

EXAMPLE 2

2-{1-[4-(4-{2-[(E)-2-(-4-Pentafluorosulfanyl-phenyl)-vinyl]-oxazol-4-ylmethoxy}-phenyl)-butyl]-1H-imidazol-2-yl}-ethanol i) 2-{1-[4-(4-Methoxy-phenyl)-butyl]-1H-imidazol-2-yl}-ethanol A mixture of 3.65 g (15.0 mmol) 1-(4-bromo-butyl)-4-methoxy-benzene, 2.52 g (22.5 mmol) 2-(1H-imidazol-2-yl)-ethanol, 2.74 g (16.5 mmol) potassium iodide, 0.90 g (22.5 mmol) sodium hydroxide and 15 ml 2-methyl-2-butanol was heated to reflux for 12 h. Solvents were distilled off, the residue dissolved in toluene and washed with water. After drying over Na₂SO₄ and removal of solvents in vacuo the residue was stirred with 7 ml ethyl acetate, isolated by filtration, washed with ethyl acetate and dried. Yield 2.41 g (59%).

MS: M=275.4 (ESI+).

ii) 4-{4-[2-(2-Hydroxyethyl)-imidazol-1-yl]-butyl}-phenol 2.40 g (8.75 mmol) 2-{1-[4-(4-methoxy-phenyl)-butyl]-1H-imidazol-2-yl}-ethanol and 9 ml (81 mmol) 48% aqueous hydrobromic acid were stirred at 80° C. for 12 h. The mixture was cooled to 0° C., 23 ml 4 N NaOH added, extracted with toluene and the aqueous phase adjusted to pH=6.3 by addition of 1 N HCl. The resulting precipitate was isolated, washed twice with water and ethyl acetate and dried. 1.71 g (75%) yellow crystals.

¹H-NMR(400 MHz, D₆-DMSO): δ=1.47 (quintet, 2H, CH₂—CH₂—Ar), 1.64 (quintet, 2H, CH₂—CH₂-imidazole), 2.48 (t, 2H, CH₂—Ar), 2.73 (t, 2H, CH₂—CH₂OH), 3.68 (q, 2H, CH₂OH), 3.88 (t, 2H, CH₂-imidazole), 4.76 (t, 1H, CH₂OH), 6.65 (d, 2H, 2'-/6'-H), 6.74 (s, 1H, imidazole), 6.95 (d, 2H, 3'-/5'-H), 7.00 (s, 1H, imidazole), 9.12(br, 1H, PhOH).

iii) 2-{1-[4-(4-{2-[(E)-2-(-4-Pentafluorosulfanyl-phenyl)-vinyl]-oxazol-4-ylmethoxy}-phenyl)-butyl]-1H-imidazol-2-yl}-ethanol 14 mg (0.50 mmol) 95% sodium hydride were given to a solution of 130 mg (0.50 mmol) 4-{4-[2-(2-Hydroxyethyl)-imidazol-1-yl]-butyl}-phenol in 4.0 ml DMF and stirred for 15 min. 168 mg (0.50 mmol) 4-chloromethyl-2-[2-(4-pentafluorosulfanyl-phenyl)-vinyl]-oxazole were added and stirring continued at r.t. overnight. After addition of 10 ml water the resulting precipitate was filtered, dried and purified by chromatography on silica (ethyl acetate/methanol 8:1) to give 133 mg (47%) amorphous material.

MS: M=570.1 (ESI+)

¹H-NMR(400 MHz, D₆-DMSO): δ=1.51 (quintet, 2H, CH₂—CH₂—Ar), 1.65 (quintet, 2H, CH₂—CH₂-imidazole), 2.53 (t, 2H, CH₂—Ar), 2.74 (t, 2H, CH₂—CH₂OH), 3.69 (q, 2H, CH₂OH), 3.89 (t, 2H, CH₂-imidazole), 4.77 (br, 1H, OH), 4.99 (s, 2H, OCH₂), 6.75 (s, 1H, imidazole), 6.95 (d, H, 2'-/6'-H, Ar—H), 7.02 (s, 1H, imidazole), 7.08 (d, 2H, 3'-/5'-H —Ar), 7.35 (d, 1H, vinyl-H), 7.61 (d, 1H, vinyl-H), 7.94 (m, 4H, ArSF₅), 8.24 (s, 1H, oxazole).

EXAMPLE 3

[4-(4-[1,2,3]Triazol-1-yl-but-1-enyl)-phenyl]-{2-[2-(4-pentafluorosulfanyl-phenyl)-vinyl]-oxazol-4-ylmethyl}-amine i) (4-Iodo-phenyl)-carbamic acid tert-butyl ester 4-Iodoaniline (3.28 g, 15 mmol) is dissolved in anhydrous THF (70 ml), cooled to 0° C. and treated with lithium hexamethyldisilazide (1M in THF, 30 ml, 30 mmol). After warming to room temperature di-tert-butyl dicarbonate (3.27 g, 15 mmol) in anhydrous THF (30 ml) is added dropwise and the mixture stirred for 2 h. The reaction is quenched by the addition of sat. NH₄Cl solution, the organic phase is separated and washed with water. After concentration the crude product is purified by flash column chromatography (ethyl acetate/heptane 4:1) yielding (4-iodo-phenyl)-carbamic acid tert-butyl ester as a tan solid (3.37 g, 70%; ~10% contamination with di-tert-butyl ester).

MS: M=318.0 (ESI−)

¹H-NMR (400 MHz, [D₆]-DMSO): δ=1.47 (s, 9H), 7.29 (d, 2H), 7.57 (d, 2H), 9.46 (s, br, NH)

ii) [4-(4-[1,2,3]Triazol-1-yl-but-1-enyl)-phenyl]-carbamic acid tert-butyl ester A solution of 1-but-3-ynyl-1H-[1,2,3]triazole (0.76 g, 6.3 mmol) in anhydrous THF (50 ml) is treated with 9-BBN (0.5 M in THF, 27.6 ml, 13.8 mmol) at 0° C. and stirred for 2 h. This mixture is added to a solution of (4-iodo-phenyl)-carbamic acid tert-butyl ester (2 g, 6.3 mmol), [Pd(PPh$_3$)$_2$]Cl$_2$ (0.51 g, 0.63 mmol) and aqueous potassium carbonate (3M, 6.3 ml, 18.8 mmol) in N,N-dimethyl formamide (50 ml) and stirred for 2 h at 70° C. After cooling to room temperature ethyl acetate (100 ml) is added and the solution extracted with water (2×50 ml). The organic layer is concentrated and the crude product purified by flash column chromatography (ethyl acetate/heptane 3:1) and washing with diethyl ether to yield [4-(4-[1,2,3]triazol-1-yl-but-1-enyl)-phenyl]-carbamic acid tert-butyl ester as beige solid (0.65 g, 33%).

MS: M=315.0 (API+)
$^1$H-NMR (400 MHz, CDCl$_3$): 1.46 (s, 9H), 2.71 (q, 2H), 4.50 (t, 2H), 6.09 (m, 1H), 6.31 (d, 1H), 7.22 (d, 2H), 7.38 (d, 2H), 7.69 (s, 1H), 8.12 (s, 1H), 9.34 (s, NH)

iii) [4-(4-[1,2,3]Triazol-1-yl-but-1-enyl)phenyl]-{2-[2-(4-pentafluorosulfanyl-phenyl)-vinyl]-oxazol-4-ylmethyl}-amine A solution of [4-(4-[1,2,3]triazol-1-yl-but-1-enyl)-phenyl]-carbamic acid tert-butyl ester (0.135 g, 0.43 mmol) in N,N-dimethyl formamide (3 ml) was treated with sodium hydride (0.012 g, 0.47 mmol) and stirred for 30 min at room temperature. After addition of 4-chloromethyl-2-[2-(4-pentafluorosulfanyl-phenyl)-vinyl]-oxazole (0.149 g, 0.43 mmol) and stirring for 12 h the reaction was quenched by the addition of a sat. NH4Cl solution (8 ml). Extraction with ethyl acetate (3×10 ml), washing with water, drying over sodium sulfate and concentration in vacuo yielded crude [4-(4-[1,2,3]triazol-1-yl-but-1-enyl)-phenyl]-{2-[2-(4-pentafluorosulfanyl-phenyl)-vinyl]-oxazol-4-ylmethyl}-carbamic acid tert-butyl ester (0.27 g) which was used in the next step without any further purification.

The crude carbamic ester was stirred in a mixture of trifluoroacetic acid/methylene chloride (1:1, 28 ml) for 2.5 h. Water (50 ml) was added and the solution was neutralized by careful addition of sodium carbonate. The organic layer was separated, washed with water and concentrated. The crude product was purified by washing with ether followed by methanol yielding [4-(4-[1,2,3]triazol-1-yl-but-1-enyl)-phenyl]-{2-[2-(4-pentafluoro-sulfanyl-phenyl)-vinyl]-oxazol-4-ylmethyl}-amine (117 mg, 52%) as a yellow solid.

MS: M=524.0 (ESI+)
$^1$H-NMR (400 MHz, D$_6$-DMSO): 2.67 (dt, 2H, CH$_2$—CH=CHAr), 4.18 (d, 2H, CH$_2$NH), 4.47 (t, 2H, CH$_2$-triazole), 5.87 (dt, 1H, =CH—CH$_2$), 6.17–6.24 (m, 2H, NH, =CH—Ar), 6.58 (d, 2H, 3'-/5'-H—Ar), 7.08 (d, 2H, 2'-/6'-H—Ar), 7.31 (d, 1H, vinyl-H), 7.55 (d, 1H, vinyl-H), 7.69 (s, 1H, triazole), 7.92 (m, 4H, ArSF$_5$), 7.99 (s, 1H, triazole), 8.11 (s, 1H, oxazole).

EXAMPLE 4

1-[4-(4-{2-[(E)-2-(-4-Pentafluorosulfanyl-phenyl)-vinyl]-oxazol-4-ylmethoxy}-phenyl)-butyl]-1H-[1,2,3]triazole 25.0 mg (1.00 mmol) 95% sodium hydride were given to a solution of 217 mg (1.00 mmol) 4-(4-[1,2,3]triazol-1-yl-butyl)-phenol in 3.0 ml DMF and stirred for 30 min. 346 mg (1.00 mmol) 4-chloromethyl-2-[2-(4-pentafluorosulfanyl-phenyl)-vinyl]-oxazole were added and stirring continued at r.t. for 24 h. After cautious addition of 10 ml water the mixture was diluted to 60 ml by further addition of water and stirred for 30 min. The resulting precipitate was washed with 3×10 ml water, 2×10 ml methanol/water, diethyl ether and dried to yield 440 mg (84%) of the title compound.

MS: M=527.0 (ESI+)
$^1$H-NMR(400 MHz, D$_6$-DMSO): δ=1.48 (quintet, 2H, CH$_2$—CH$_2$—Ar), 1.81 (quintet, 2H, CH$_2$—CH$_2$-triazole), 2.53 (t, 2H, CH$_2$—Ar), 4.40 (t, 2H, CH$_2$-triazole), 4.99 (s, 2H, OCH$_2$-oxazole), 6.95 (d, 2H, 3'-/5'-H—Ar), 7.10 (d, 2H, 2'-/6'-H—Ar) 7.35 (d, 1H, vinyl-H), 7.61 (d, 1H, vinyl-H), 7.71 (s, 1H, triazole), 7.94 (m, 4H, ArSF$_5$), 8.11 (s, 1H, triazole), 8.25 (s, 1H, oxazole).

EXAMPLE 5

4-[4-(4-{2-[(E)-2-(-4-Pentafluorosulfanyl-phenyl)-vinyl]-oxazol-4-ylmethoxy}-phenyl)-butyl]-1H-[1,2,3]triazole i) 1-(4-Iodo-butyl)-4-methoxy-benzene A mixture consisting of 30.2 g (124 mmol) 1-(4-bromo-butyl)-4-methoxy-benzene, 19.2 g (128 mmol) sodium iodide and 508 ml acetone was heated to reflux temperature for 1 h. The resulting suspension was cooled to r.t. and the precipitated sodium bromide removed by filtration. The filtrate was stripped off the solvents by vacuum distillation and the residue distributed between water and diethyl ether. After drying of the organic phase over sodium sulphate, vacuum distillation gave 34.9 g (97%) of the title compound as slightly yellow coloured liquid.

MS: M=290.0 (ESI).

ii) [6-(4-Methoxy-phenyl)-hex-1-ynyl]-trimethyl-silane 12.4 ml (19.8 mmol) of 1.6 M butyllithium in n-hexane was added dropwise at −78° C. to a solution of 1.94 g (2.80 ml, 19.8 mmol) trimethylsilylacetylene and 2.39 ml(19.8 mmol) DMPU in 30 ml THF. After stirring for 1 h at −78° C. a solution of 28.7 g (9.89 mmol) 1-(4-Iodo-butyl)-4-methoxy-benzene in ml THF was added at −78° C. and stirring continued for 30 min. The reaction mixture was allowed to warm to r.t. overnight and then hydrolyzed by a saturated ammonium chloride solution. The water phase was extracted with ether and the combined organic phases were dried over sodium sulphate. Removal of solvents in vacuo gave 3.20 g yellow liquid, which still contained solvent and was used without further purification.

MS: M=260.1 (ESI).
$^1$H-NMR(400 MHz, CDCl$_3$): δ=0.15 (s, 9H, Si(CH$_3$)$_3$), 1.57 (quintet, 2H, CH$_2$—CH$_2$—C≡CH), 1.70 (quintet, 2H, CH$_2$—CH$_2$—Ar), 1.93 (s, 1H, ≡CH), 2.19 (t, 2H, CH$_2$—C≡CH), 2.59 (t, 2H, CH$_2$—Ar), 3.78 (s, 3H, OCH$_3$), 6.81 (d, 2H, 3'-/5'-H), 7.08 (d, 2H, 2'-H/$_6$'-H).

iii) 1-Hex-5-ynyl-4-methoxy-benzene

A mixture of 3.20 g (12.3 mmol) [6-(4-methoxy-phenyl)-hex-1-ynyl]-trimethyl-silane, 50 ml methanol and 12.3 ml (24.6 mmol) 2N NaOH was stirred for 2 h at r.t. After neutralization with 13 ml 2N HCl methanol was distilled off and the aqueous phase extracted with diethyl ether. Drying (Na$_2$SO$_4$) and removal of solvents in vacuo gave 1.80 g (78%) of the title compound.

MS: M=188.1 (ESI).

$^1$H-NMR(400 MHz, CDCl$_3$): δ=1.55 (quintet, 2H, CH$_2$—CH$_2$—C≡C), 1.69 (quintet, 2H, CH$_2$—CH$_2$—Ar), 2.26 (t, 2H, CH$_2$—C≡C), 2.60 (t, 2H, CH$_2$—Ar), 3.78 (s, 3H, OCH$_3$), 6.83 (d, 2H, 3'-/5'-H), 7.09 (d, 2H, 2'-H/6'-H).

iv) 4-(4-(4-Methoxy-phenyl)-butyl)-1H-[1,2,3]triazole

A mixture of 1.80 g (9.56 mmol) 1-hex-5-ynyl-4-methoxy-benzene, 1.86 g (28.6 mmol) sodium azide, 1.53 g (28.6 mmol) ammonium chloride and 80 ml DMF was kept at 125° C. for 7 d with an extra addition of 1.80 g sodium azide and 1.53 g ammonium chloride every day. After cooling to r.t. the dark reaction mixture was distributed between water and ethyl acetate. The organic phase was dried over sodium sulphate and the solvent distilled off. The residue was separated by HPLC on a RP18-endcapped column (methanol/water) (a reversed phase column which is used with methanol/water as eluent) to yield 450 mg 5-(4-(4-Methoxy-phenyl)-butyl)-2H-tetrazole and 500 mg 4-(4-(4-Methoxy-phenyl)-butyl)-1H-[1,2,3]triazole 5-(4-(4-Methoxy-phenyl)-butyl)-2H-tetrazole

MS: M=233.3(APCI+), 231.3(APCI−).

$^1$H-NMR(400 MHz, CDCl$_3$): δ=1.67 (quintet, 2H, CH$_2$—CH$_2$—Ar), 1.87 (quintet, 2H, CH$_2$—CH$_2$-tetrazole), 2.56 (t, 2H, CH$_2$—Ar), 3.08 (t, 2H, CH$_2$-tetrazole), 3.74 (s, 3H, OCH$_3$), 6.76 (d, 2H, 3'-/5'-H), 6.97 (d, 2H, 2'-/6'-H), 11.5–12.5 (br, 1H, NH).

4-(4-(4-Methoxy-phenyl)-butyl)-1H-[1,2,3]triazole

MS: M=232.2(APCI+), 230.2(APCI−).

$^1$H-NMR(400 MHz, D$_6$-DMSO): δ=1.50–1.65 (m, 4H), 2.53 (t, 2H, CH$_2$—Ar), 2.65 (t, 2H, CH$_2$-triazole), 3.71 (s, 3H, OCH$_3$), 6.83 (d, 2H, 3'-/5'-H), 7.08 (d, 2H, 2'-/6'-H), 7.5 (br, 1H, 5-H-triazole), 14–15 (br, 1H, NH).

v) 4-(4-1H-[1,2,3]triazol-4-yl-butyl)-phenol

A mixture of 500 mg 4-(4-(4-methoxy-phenyl)-butyl)-1H-[1,2,3]triazole and 1.5 ml 48% hydrobromic acid was stirred at 80° C. for 9 h. After adjustment to pH=6 by addition of conc. sodium hydroxide solution, the aqueous layer was discarded and the remaining sticky residue purified by HPLC-MS(RP18, methanol/water 7:3, pH=2.3). Yield 170 mg (36%).

MS: M=218.2(APCI+), 216.2(APCI−).

$^1$H-NMR(400 MHz, D$_6$-DMSO): δ=1.55 (mc, 4H, CH$_2$), 2.48 (t, 2H, CH$_2$—Ar), 2.64 (t, 2H, CH$_2$-triazole), 6.65 (d, 2H, 2'-/6'-H), 6.95 (d, 2H, 3'-/5'-H), 7.58 (br, 1H, 5-H-triazole), 9.08 (br, 1H, NH).

vi) 4-[4-(1-Trityl-1H-[1,2,3]triazol-4-yl)-butyl]-phenol

A solution of 706 mg (5.06 mmol) triphenylchloromethane in 5.0 ml DMF was added at 0° C. to a solution of 500 mg (2.30 mmol) 4-(4-1H-[1,2,3]triazol-4-yl-butyl)-phenol and 512 mg (5.06 mmol) triethylamine in 5.0 ml DMF. The mixture was allowed to reach r.t. overnight and solvents were removed in vacuo. After distribution of the residue between water and ethyl acetate, the organic phase was dried (sodium sulphate), solvents distilled off and the residue purified by column chromatography on silica gel (heptane/ethyl acetate 2:1).

Yield 610 mg (58%).

MS: M=460.2(ESI+), 482.2 (ESI+, M+Na$^+$), 458.2 (ESI−).

$^1$H-NMR(400 MHz, CDCl$_3$): δ=1.59 (mc, 2H, CH$_2$—CH$_2$—Ar), 1.67 (mc, 2H, CH$_2$—CH$_2$-triazole), 2.53 (t, 2H, CH$_2$—Ar), 2.71 (t, 2H, CH$_2$-triazole), 5.10 (s, 1H, OH), 6.72(d, 2 H, 2'-/6'-H), 6.97 (d, 2H, 3'-/5'-H), 7.05–7.40 (m, 15H, trityl).

vii) 4-[4-(4-{2-[(E)-2-(-4-Pentafluorosulfanyl-phenyl)-vinyl]-oxazol-4-ylmethoxy}-phenyl)-butyl]-1-trityl-1H-[1,2,3]triazole 7.8 mg (0.20 mmol) 95% sodium hydride were given at 0° C. to a solution of 90 mg (0.20 mmol) 4-[4-(1-trityl-1H-[1,2,3]triazol-4-yl)-butyl]-phenol in 3.0 ml N,N-dimethylformamide and stirred for 15 min. 66 mg (0.20 mmol) 4-chloromethyl-2-[2-(4-pentafluorosulfanyl-phenyl)-vinyl]-oxazole were added and stirring continued at 25° C. for 2 h. The reaction mixture was poured into water, the precipitate isolated by filtration und purified by LC-MS to yield 98 mg (65%) of the title compound

MS: M=769.07(APCI+).

viii) 4-[4-(4-{2-[(E)-2-(-4-Pentafluorosulfanyl-phenyl)-vinyl]-oxazol-4-ylmethoxy}-phenyl)-butyl]-1H-[1,2,3]triazole A mixture of 98 mg 4-[4-(4-{2-[(E)-2-(-4-pentafluorosulfanyl-phenyl)-vinyl]-oxazol-4-ylmethoxy}-phenyl)-butyl]-1-trityl-1H-[1,2,3]triazole, 100 μl formic acid, 10 μl water and 1.0 ml tetrahydrofuran was stirred at 60° C. for 21 h. After removal of solvents in vacuo 4-[4-(4-{2-[(E)-2-(4-pentafluorosulfanyl-phenyl)-vinyl]-oxazol-4-ylmethoxy}-phenyl)-butyl]-1H-[1,2,3]triazole was obtained by HPLC-MS-purification.

MS: M=527.1(APCI+), 525.1(APCI−).

$^1$H-NMR(400 MHz, D$_6$-DMSO): δ=1.58 (m, 4H), 2.54 (t, 2H, CH$_2$—Ar), 2.65 (t, 2H, CH$_2$-triazole), 4.99 (s, 2H, OCH$_2$), 6.94 (d, 2H, 3'-/5'-H), 7.11 (d, 2H, 2'-/6'-H), 7.57 (br, 1H, triazole), 7.61 (d, 1H, vinyl-H), 7.94 (s, 4H, ArSF$_5$), 8.26 (s, 1H, oxazole).

EXAMPLE 6

5-[4-(4-{2-[(E)-2-(-4-Pentafluorosulfanyl-phenyl)-vinyl]-oxazol-4-ylmethoxy}-phenyl)-butyl]-2H-tetrazole i) 4-(4-2H-tetrazol-5-yl-butyl)-phenol 450 mg (1.94 mmol) 5-(4-(4-methoxy-phenyl)-butyl)-2H-tetrazole and 1.5 ml 48% aqueous hydrobromic acid were stirred at 80° C. for 17 h. The reaction mixture was adjusted to pH=4 by addition of conc. NaOH and the aqueous phase discarded. Purification of the undissolved residue by HPLC-MS (methanol/water 7:3, pH=2.3) gave 220 mg (52%) of the title compound.

MS: M=219.3(APCI+), 217.3(APCI−).

$^1$H-NMR(400 MHz, D$_6$-DMSO): δ=1.53 (quintet, 2H, CH$_2$—CH$_2$—Ar), 1.68 (quintet, 2H, CH$_2$—CH$_2$-tetrazole), 2.48 (t, 2H, CH₂—Ar), 2.89 (t, 2H, CH₂-tetrazole), 6.65 (d, 2H, 2'-/6'-H), 6.96 (d, 2H, 3'-/5'-H), 9.1 (br, 1H, OH), 16 (br, 1H, NH).

ii) 5-[4-(4-{2-[(E)-2-(-4-Pentafluorosulfanyl-phenyl)-vinyl]-oxazol-4-ylmethoxy}-phenyl)-butyl]-2H-tetrazole 46.3 mg (1.84 mmol) 95% sodium hydride were given at 0° C. to a solution of 200 mg (0.916 mmol) 4-(4-tetrazol-5-yl-butyl)-phenol in 5.0 ml N,N-dimethylformamide and stirred for 15 min. 317 mg (0.916 mmol) 4-chloromethyl-2-[2-(4-pentafluorosulfanyl-phenyl)-vinyl]-oxazole were added and stirring continued at 25° C. for 2 h. The reaction mixture was neutralized with HCl, poured into water and the resulting precipitate was purified by HPLC-MS, treated with diethyl ether, filtered and dried to yield 106 mg (22%) of the title compound.

MS: M=528.2 (ESI+), 526.2 (ESI−).

¹H-NMR(400 MHz, D₆-DMSO): δ=1.57 (quintet, 2H, CH₂—CH₂—Ar), 1.69 (quintet, 2H, CH₂—CH₂-tetrazole), 2.54 (t, 2H, CH₂—Ar), 2.89 (t, 2H, CH₂-tetrazole), 4.99 (s, 3H, OCH₃), 6.95 (d, 2H, 2'-/6'-H), 7.11 (d, 2H, 3'-/5'-H), 7.35 (d, 1H, vinyl-H), 7.61 (d, 1H, vinyl-H), 7.94 (m, 4H, ArSF₅), 8.25 (s, 1H, oxazole).

EXAMPLE 7

2-{5-[4-(4-{2-[2-(4-Pentafluorosulfanyl-phenyl)-vinyl]-oxazol-4-ylmethoxy}-phenyl)-butyl]-tetrazol-1-yl}-ethanol 6.4 mg (0.16 mmol) 95% sodium hydride were added to a solution of 82.0 mg (0.156 mmol) 5-[4-(4-{2-[(E)-2-(-4-pentafluorosulfanyl-phenyl)-vinyl]-oxazol-4-ylmethoxy}-phenyl)-butyl]-2H-tetrazole in 2.0 ml DMF and stirred for 15 min. 19.8 mg (0.159 mmol) 2-bromoethanol were added, the mixture stirred overnight and evaporated. Separation by LC-MS (methanol/water 3:1, pH=2.3) on a C4 reversed phase column (YMC-PACK® C4 (Butyl) reversed phase column from YMC Europe GmbH, Schermbeck, Germany) gave 32 mg of the title compound and 6 mg of 2-{5-[4-(4-{2-[2-(4-Pentafluorosulfanyl-phenyl)-vinyl]-oxazol-4-ylmethoxy}-phenyl)-butyl]-tetrazol-2-yl}-ethanol (example 8).

EXAMPLE 8

2-{5-[4-(4-{2-[2-(4-Pentafluorosulfanyl-phenyl)-vinyl]-oxazol-4-ylmethoxy}-phenyl)-butyl]-tetrazol-2-yl}-ethanol 6.4 mg (0.16 mmol) 95% sodium hydride were added to a solution of 82.0 mg (0.156 mmol) 5-[4-(4-{2-[(E)-2-(-4-pentafluorosulfanyl-phenyl)-vinyl]-oxazol-4-ylmethoxy}-phenyl)-butyl]-2H-tetrazole in 2.0 ml DMF and stirred for 15 min. 19.8 mg (0.159 mmol) 2-bromoethanol were added, the mixture stirred overnight and evaporated. Separation by LC-MS (methanol/water 3:1, pH=2.3) on a C4 reversed phase column gave 6 mg of the title compound and 32 mg of 2-{5-[4-(4-{2-[2-(4-Pentafluorosulfanyl-phenyl)-vinyl]-oxazol-4-ylmethoxy}-phenyl)-butyl]-tetrazol-1-yl}-ethanol (example 7).

EXAMPLE 9

1-[2-(4-{2-[-4-(Pentafluorosulfanyl-phenyl)-vinyl]-oxazol-4-ylmethoxy}-benzyloxy)-ethyl]-1H-[1,2,3]-triazole i) 1-Allyloxy-4-chloromethyl-benzene 7.67 g (67.0 mmol) methanesulfonyl chloride were given at 0° C. to a solution of 10.0 g (60.9 mmol) (4-allyloxy-phenyl)-methanol and 9.34 ml (67.0 mmol) triethylamine in 35 ml dichloromethane and stirred at r.t. overnight. The mixture was poured in ice water, extracted with dichloromethane and the organic phase dried over Na₂SO₄. After removal of solvents the residue was purified by chromatography on silica gel (ethyl acetate/n-heptane 1:5) to yield 3.12 g (28%) pale yellow oil.

¹H-NMR(400 MHz, D₆-DMSO): δ=4.57 (m, 2H, OCH₂), 4.72 (s, 2H, CH₂Cl), 5.26 (d, 1H, =CH₂), 5.39 (d, 1H, =CH₂), 6.04 (m, 1H, CH=CH₂), 6.95 (d, 2H, 2'-/6'-H), 7.35 (d, 2H, 3'-/5'-H).

ii) 1-[2-(4-Allyloxy-benzyloxy)-ethyl]-1H-[1,2,3]-triazole 197 mg 8.21 mmol) 95% sodium hydride were given at −50° C. to a solution of 1.00 g (5.47 mmol) 1-allyloxy-4-chloromethyl-benzene and 619 mg (5.47 mmol) 2-(1H-[1,2,3]-triazol-1-yl)-ethanol in 9.0 ml DMF. The mixture was allowed to warm slowly to r.t., stirred overnight and 10 ml water added. The formed oil was collected with 10 ml dichloromethane, the aqueous phase extracted with 10 ml dichloromethane and the combined organic phases dried over Na₂SO₄.

Solvents were removed in vacuum and the residue purified by chromatography on silica gel (ethyl acetate/heptane 1:1) to yield 1.10 g (78%) yellow oil.

MS: M=260.3 (APCI+), 258.3 (APCI−).

¹H-NMR(400 MHz, D₆-DMSO): δ=3.79 (t, 2H, CH₂—CH₂-triazole), 4.39 (s, 2H, OCH₂Ph), 4.54–4.59 (m, 4H, OCH₂-vinyl, CH₂-triazole), 5.25 (d, 1H, =CH₂), 5.38 (d, 1H, =CH₂), 6.06 (m, 1H, CH=CH₂), 6.89 (d, 2H, 2'-/6'-H), 7.15 (d, 2H, 3'-/5'-H), 7.16 (s, 1H, triazole), 8.08 (s, 1H, triazole).

iii) 4-(2-[1,2,3]Triazol-1-yl-ethoxymethyl)-phenol

A solution of 500 mg (1.93 mmol) 1-[2-(4-allyloxy-benzyloxy)-ethyl]-1H-[1,2,3]-triazole in 10 ml dichloromethane was added to a solution of 904 mg (5.79 mmol) 1,3-dimethylbarbituric acid and 58 mg (0.05 mmol) Pd(PPh₃)₄ in 20 ml dichloromethane and stirred for 4.5 h at 40° C. The mixture was extracted with 3×20 ml sat. NaHCO₃-solution and 8 ml water and the combined aqueous phases were reextracted with 2×10 ml dichloromethane. The organic extracts were combined and dried over MgSO₄. Solvents were distilled off and the residue purified by chromatography on silica gel (ethyl acetate) to yield 248 mg (59%) of the title compound.

¹H-NMR(400 MHz, D₆-DMSO): δ=3.77 (t, 2H, CH₂—CH₂-triazole), 4.33 (s, 2H, OCH₂Ph), 4.56 (t, 2H, CH₂-triazole), 6.69 (d, 2H, 2'-/6'-H), 7.03 (d, 2H, 3'-/5'-H), 7.11 (s, 1H, triazole), 8.07 (s, 1H, triazole), 9.37 (s, 1H, PhOH).

iv) 1-[2-(4-{2-[(E)-2-(-4-Pentafluorosulfanyl-phenyl)-vinyl]-oxazol-4-ylmethoxy}-phenyl-methoxy)-ethyl]-1H-[1,2,3]triazole 14 mg (0.50 mmol) 95% sodium hydride were given to a solution of 110 mg (0.50 mmol) 4-(2-[1,2,3]Triazol-1-yl-ethoxymethyl)-phenol in 4.0 ml DMF and stirred for 15 min. 173 mg (0.50 mmol) 4-chloromethyl-2-[2-(4-pentafluorosulfanyl-phenyl)-vinyl]-oxazole were added and stirring continued at r.t. overnight. After addition of 10 ml water the resulting precipitate was washed twice with 10 ml water, 2×10 ml methanol, diethyl ether and dried at 45° C. in vacuum. Yield 155 mg (59%) colorless powder.

MS: M=529.1 (ESI+)

$^1$H-NMR(400 MHz, D$_6$-DMSO): δ=3.80 (t, 2H, CH$_2$—CH$_2$-triazole), 4.40 (s, 2H, OCH$_2$—Ph), 4.58 (t, 2H, CH$_2$-triazole), 5.02 (s, 2H, OCH$_2$-oxazole), 6.99 (d, 2H, 3'-/5'-H—Ar), 7.18 (d, 2H; 2H, 2'-/6'-H—Ar) 7.35 (d, 1H, vinyl-H), 7.61 (d, 1H, vinyl-H), 7.72 (s, 1H, triazole), 7.94 (m, 4H, ArSF$_5$), 8.08 (s, 1H, triazole), 8.26 (s, 1H, oxazole).

EXAMPLE 10

1-[2-(4-{2-[(E)-2-(4-Pentafluorosulfanyl-phenyl)-vinyl]-oxazol-4-ylmethoxy}-phenylmethanesulfinyl)-ethyl]-1H-[1,2,3]triazole i) (4-Allyloxy-phenyl)-methanethiol

A mixture of 2.00 g (10.9 mmol) 1-allyloxy-4-chloromethyl-benzene and 917 mg (12.1 mmol) thiourea in 3.0 ml ethanol was heated to reflux for 7 h. Solvents were distilled off and the crystalline residue was washed with cold ethanol and isolated by filtration. After addition of 2.5 ml ethanol, 1.0 ml water and 0.7 ml 25% aqueous ammonia, the mixture was heated to reflux for 1 h. Ethanol was distilled off, then acidified with 0.5 ml half conc. HCl and extracted with ethyl acetate. The solution was dried over MgSO4 and solvents were removed in vacuum to yield 1.59 g (81%) colorless oil, which was used immediately.

$^1$H-NMR(400 MHz, D$_6$-DMSO): δ=2.75 (s, 1H, SH), 3.68 (s, 2H, CH$_2$SH), 4.54 (m, 2H, OCH$_2$-vinyl), 5.26 (d, 1H, =CH$_2$), 5.38 (d, 1H, =CH$_2$), 6.05 (m, 1H, CH=CH$_2$), 6.89 (d, 2H, 2'-/6'-H), 7.24 (d, 2H, 3'-/5'-H).

ii) Toluene-4-sulfonic acid 2-[1,2,3]triazol-1-yl-ethyl ester

A solution of 12.9 g (66.3 mmol) p-toluenesulfonic acid chloride, 2.03 g (16.6 mmol) 4-(N,N-dimethylamino)-pyridine and 11.2 ml (80.2 mmol) triethylamine in 150 ml dichloromethane was cooled to −10° C. A solution of 7.50 g (66.3 mmol) 2-(1H-[1,2,3]triazol-1-yl)-ethanol in 150 ml dichloromethane was added dropwise and the mixture stirred overnight at −4° C. 170 ml Ice and 170 ml dichloromethane were added and stirring continued for 10 min. followed by addition of 3.9 ml conc. HCl. The organic phase was separated, washed with sat. NaHCO$_3$-solution and brine, dried over Na$_2$SO$_4$ and solvents distilled off. Yield 15.3 g (86%) orange crystals.

$^1$H-NMR(400 MHz, D$_6$-DMSO): δ=2.41 (s, 3H, CH$_3$), 4.41 (t, 2H, CH$_2$—OTos), 4.67 (t, 2H, CH$_2$-triazole), 7.44 (d, 2H, Ar—H), 7.65 (d, 2H, Ar—H), 7.69 (s, 1H, triazole), 8.03 (s, 1H, triazole).

iii) 1-[2-(4-Allyloxy-benzylsulfanyl)-ethyl]-1H-[1,2,3]triazole 1.58 g (6.14 mmol) (4-allyloxy-phenyl)-methanethiol and 1.64 g (6.14 mmol) toluene-4-sulfonic acid 2-[1,2,3]triazol-1-yl-ethyl ester were dissolved in 15 ml DMF and cooled to −30° C. 294 mg (12.3 mmol) 95% Sodium hydride were added, the mixture allowed to warm to r.t. and stirred for 12 h. 10 ml Water were added and the residue dissolved in dichloromethane. The organic phase was dried over Na$_2$SO$_4$, solvents removed and the remaining material purified by chromatography on silica gel (ethyl acetate/n-heptane 1:1) to yield 1.33 g (79%) yellow oil.

MS: M=298.0 (M+Na$^+$, APCI+).

$^1$H-NMR(400 MHz. D$_6$-DMSO): δ=2.86 (t, 2H, CH$_2$—CH$_2$-triazole), 3.65 (s, 2H, OCH$_2$Ph), 4.55 (m, 4H, OCH$_2$-vinyl, CH$_2$-triazole), 5.25 (d, 1H, =CH$_2$), 5.38 (d, 1H, =CH$_2$), 6.05 (m, 1H, CH=CH$_2$), 6.90 (d, 2H, 2'-/6'-H), 7.22 (d, 2H, 3'-/5'-H), 7.73 (s, 1H, triazole), 8.12 (s, 1H, triazole).

iv) 1-[2-(4-Allyloxy-phenylmethanesulfinyl)-ethyl]-1H-[1,2,3]triazole

A solution of 1.86 g (8.29 mmol) 77% 3-chloroperbenzoic acid in 40 ml ethyl acetate was added at −30° C. within 20 min. to a solution of 1.90 g (6.90 mmol) 1-[2-(4-allyloxy-benzylsulfanyl)-ethyl]-1H-[1,2,3]triazole in 160 ml dichloromethane and stirred for 1 h. The mixture was allowed to warm to r.t. washed with sat. NaHCO$_3$-solution, water and evaporated. The residue purified by chromatography on silica gel (ethyl acetate/methanol 5:1) to give 1.25 g of the title compound as white powder.

MS: M=(ESI+)

$^1$H-NMR(400 MHz, D$_6$-DMSO): δ=3.11 (dt, 1H, CH$_2$—CH$_2$-triazole), 3.32 (dt, 1H, CH$_2$—CH$_2$-triazole), 3.94.1 (d, 1H, SO$_2$CH$_2$Ph), 4.12 (d, 1H, SO$_2$CH$_2$Ph), 4.56 (d, 2H, OCH$_2$-vinyl), 4.78 (m, 2H, CH$_2$-triazole), 5.26 (d, 1H, =CH$_2$), 5.39 (d, 1H, =CH$_2$), 6.02 (m, 1H, CH=CH$_2$), 6.95 (d, 2H, 2'-/6'-H), 7.22 (d, 2H, 3'-/5'-H), 7.75 (s, 1H, triazole), 8.16 (s, 1H, triazole).

v) 4-(2-[1,2,3]Triazol-1-yl-ethanesulfinylmethyl)-phenol

A solution of 1.00 g (3.43 mmol) 1-[2-(4-Allyloxy-phenylmethanesulfinyl)-ethyl]-1H-[1,2,3]triazole in 60 ml dichloromethane was added to a solution of 1.61 g (10.3 mmol) 1,3-dimethylbarbituric acid and 102 mg (0.09 mmol) Pd(PPh$_3$)$_4$ in 30 ml dichloromethane and stirred for 5 h at 50° C. The mixture was extracted with 3×50 ml sat. NaHCO$_3$-solution and 20 ml water. Thee organic phase was discarded and the aqueous phase acidified with 2M HCl to pH=4, concentrated to volume of 50 ml and adjusted to pH=1. After five extractions with ethyl acetate, the organic extracts were combined and dried over MgSO$_4$. After evaporation the residue was purified by chromatography on silica gel (dichloromethane/methanol 100:2) to yield 0.84 g (97%) of the title compound.

$^1$H-NMR(400 MHz, D$_6$-DMSO): δ=3.11 (dt, 1H, CH$_2$—CH$_2$-triazole), 3.29 (dt, 1H, CH$_2$—CH$_2$-triazole), 3.90 (d, 1H, SOCH$_2$Ph), 4.06 (d, 1H, SOCH$_2$Ph), 4.77 (m, 2H, CH$_2$-triazole), 6.74 (d, 2H, 2'-/6'-H), 7.10 (d, 2H, 3'-/5'-H), 7.74 (s, 1H, triazole), 8.16 (s, 1H, triazole), 9.49 (s, 1H, OH).

vi) 1-[2-(4-{2-[(E)-2-(-4-Pentafluorosulfanyl-phenyl)-vinyl]-oxazol-4-ylmethoxy}-phenyl-methanesulfinyl)-ethyl]-1H-[1,2,3]triazole 14 mg (0.50 mmol) 95% sodium hydride were given to a solution of 126 mg (0.50 mmol) 4-(2-[1,2,3]Triazol-1-yl-ethanesulfinylmethyl)-phenol in 3.0 ml DMF and stirred for 15 min. 173 mg (0.50 mmol) 4-chloromethyl-2-[2-(4-pentafluorosulfanyl-phenyl)-vinyl]-oxazole were added and stirring continued at r.t. overnight. After addition of 6 ml water the resulting precipitate was washed with water (2×), water/methanol 1:1 (2×), ethyl acetate/n-heptane 3:1 (1×), little ethyl acetate (1×), diethyl ether (1×) and dried in vacuum at 40° C. Further purification by chromatography on silica gel (eluent:ethyl acetate/methanol 15:1) and stirring of the isolated product with little ether and ethyl acetate and drying gave 48 mg (17%) white powder.

MS: M=561.0 (ESI+), 583.0(M+Na+, ESI+).

$^1$H-NMR(400 MHz, D$_6$-DMSO): δ=3.12 (dt, 1H, CH$_2$—CH$_2$-triazole), 3.30 (dt, 1H, CH$_2$—CH$_2$-triazole), 3.96 (d, 1H, SOCH$_2$Ph), 4.14 (d, 1H, SOCH$_2$Ph), 4.79(m, 2H, CH$_2$-triazole), 7.05 (d, 2H, 3'-/5'-H—Ar), 7.25 (d, 2H; 2H, 2'-/6'-H—Ar), 7.35 (d, 1H, vinyl-H), 7.61 (d, 1H, vinyl-H), 7.75 (s, 1H, triazole), 7.94 (m, 4H, ArSF$_5$), 8.17 (s, 1H, triazole), 8.27(s, 1H, oxazole).

EXAMPLE 11

1-[2-(4-{2-[(E)-2-(4-Pentafluorosulfanyl-phenyl)-vinyl]-oxazol-4-ylmethoxy}-phenylmethanesulfonyl)-ethyl]-1H-[1,2,3]triazole i) 1-[2-(4-Allyloxy-phenylmethanesulfonyl)-ethyl]-1H-[1,2,3]triazole

A solution of 13.3 g (21.6 mmol) oxone in 80 ml water was added within 20 min. to a solution of 2.00 g (7.20 mmol) 1-[2-(4-allyloxy-benzylsulfanyl)-ethyl]-1H-[1,2,3]triazole in 160 ml methanol and stirred for 24 h. The formed precipitate was dissolved in dichloromethane, washed with NaHCO$_3$-solution and dried over Na$_2$SO$_4$. Solvents were removed and the residue purified by chromatography on silica gel (ethyl acetate) to give the title compound as white powder.

MS: M=308.3 (APCI+), 330.3 (M+Na+, APCI+).

$^1$H-NMR(400 MHz, D$_6$-DMSO): δ=3.68 (t, 2H, CH$_2$—CH$_2$-triazole), 4.41 (s, 2H, SO$_2$CH$_2$Ph), 4.57 (d, 2H, OCH$_2$-vinyl), 4.80 (t, 2H, CH$_2$-triazole), 5.26 (d, 1H, =CH$_2$), 5.39 (d, 1H, =CH$_2$), 6.04 (m, 1H, CH=CH$_2$), 6.98 (d, 2H, 2'-/6'-H), 7.29 (d, 2H, 3'-/5'-H), 7.74 (s, 1H, triazole), 8.18 (s, 1H, triazole).

ii) 4-(2-[1,2,3]Triazol-1-yl-ethanesulfonylmethyl)-phenol

A solution of 2.39 g (7.78 mmol) 1-[2-(4-allyloxy-phenylmethanesulfonyl)-ethyl]-1H-[1,2,3]triazole in 50 ml dichloromethane was added to a solution of 3.64 g (23.3 mmol) 1,3-dimethylbarbituric acid and 220 mg (0.19 mmol) Pd(PPh$_3$)$_4$ in 90 ml dichloromethane and stirred for 7 h at 40° C. The reaction mixture was washed with 3×80 ml sat. NaHCO$_3$-solution, 2×30 ml water and the water phase extracted with 2×80 ml dichloromethane. The remaining precipitate was collected, washed with water and ethyl acetate and dried to yield. All dichloromethane fractions were combined, dried over 0.86 g of product. The aqueous phase from above was acidified by acetic acid to pH=5 and extracted with ethyl acetate. After washing with water and drying over sodium sulphate the ethyl acetate extract was evaporated to give 1.45 g of an orange powder that was purified by chromatography on silica gel (eluent:ethyl acetate) to yield an additional amount of 0.47 g product. Combined yield: 1.33 g (58%).

MS: M=268.3 (ESI+), 290.3 (M+Na+, ESI+).

$^1$H-NMR(400 MHz, D$_6$-DMSO): δ=3.66 (t, 2H, CH$_2$—CH$_2$-triazole), 4.34 (s, 2H, SO$_2$CH$_2$Ph), 4.79 (t, 2H, CH$_2$-triazole), 6.77 (d, 2H, 2'-/6'-H), 7.17 (d, 2H, 3'-/5'-H), 7.74 (s, 1H, triazole), 8.18(s, 1H, triazole), 9.62 (br, 1H, OH).

iii) 1-[2-(4-{2-[(E)-2-(-4-Pentafluorosulfanyl-phenyl)-vinyl]-oxazol-4-ylmethoxy}-phenyl-methanesulfonyl)-ethyl]-1H-[1,2,3]triazole 14.0 mg (0.50 mmol) 95% sodium hydride were given to a solution of 134 mg (0.50 mmol) 4-(2-[1,2,3]Triazol-1-yl-ethanesulfonylmethyl)-phenol in 4.0 ml DMF and stirred for 15 min. 173 mg (0.50 mmol) 4-chloromethyl-2-[2-(4-pentafluorosulfanyl-phenyl)-vinyl]-oxazole were added and stirring continued at r.t. overnight. After addition of 10 ml water the resulting precipitate was purified by chromatography on silica gel (eluent:ethyl acetate/n-heptane 1:1) to yield 58 mg (20%) pale yellow powder.

MS: M=577.0 (ESI+), 599.0(M+Na+, ESI+).

$^1$H-NMR(400 MHz, CDCl$_3$): δ=3.53 (t, 2H, CH$_2$—CH$_2$-triazole), 4.08 (s, 2H, SO$_2$CH$_2$—Ph), 4.89 (t, 2H, CH$_2$-triazole), 5.05 (s, 2H, OCH$_2$-oxazole), 7.02 (d, 2H, 3'-/5'-H—Ar), 7.27 (d, 2H; 2H, 2'-/6'-H—Ar) 7.53 (d, 1H, vinyl-H), 7.59 (d, 2H, ArSF$_5$), (d, 1H, vinyl-H), (s, 1H, triazole), 7.94 (d, 2H, ArSF$_5$), (s, 1H, triazole), (s, 1 H, oxazole).

$^1$H-NMR(400 MHz, D$_6$-DMSO): δ=3.70 (t, 2H, H$_2$CH$_2$-triazole), 4.42 (s, 2H, SO$_2$CH$_2$—Ph), 4.82 (t, 2H, CH$_2$-triazole), 5.05 (s, 2H, OCH$_2$-oxazole), 7.03 (d, 2H, 3'-/5'-H—Ar), 7.08 (d, 2H, 2'-/6'-H—Ar), 7.61 (d, 1H, vinyl-H), 7.84 (s, 1H, triazole), 7.94 (m, 5H, ArSF$_5$, triazole), 8.28 (s, 1H, oxazole).

EXAMPLE 12

1-[4-(4-{2-[2-(4-Pentafluorosulfanyl-phenyl)-vinyl]-oxazol-4-ylmethoxy}-phenyl)-but-3-enyl]-1H-[1,2,3]triazole i) 1-But-3-enyl-1H-[1,2,3]triazole

1H-[1,2,3]Triazole (10.36 g, 0.15 mol), sodium hydroxide (6 g, 0.15 mol) and potassium iodide (2.49 g, 0.015 mol) were dissolved in 2-methyl-2-butanol (50 ml) and heated to reflux for 1 h. At this temperature 4-bromo-but-1-ene (20.25 g, 0.15 mol) in 2-methyl-2-butanol (20 ml) were added dropwise and the resulting mixture was heated at reflux temperature for 4 h. After removal of the solvent the residue was taken up in ethyl acetate (100 ml), washed with water (3×50 ml), dried over sodium sulfate and concentrated. The crude product was purified by destillation yielding 0.65 g 2-but-3-enyl-2H-[1,2,3]triazole (b.p. 90-100° C. at 10 mbar), $^1$H-NMR (400 MHz, [D$_6$]-DMSO): δ=2.62 (q, 2H, CH$_2$—CH=CH$_2$), 4.48 (t, 2H, CH$_2$-triazole), 4.97–5.06 (m, 2H, CH$_2$—CH=CH$_2$), 5.75 (m, 1H, CH$_2$—CH=CH$_2$), 7.75 (s, 2H, triazole) and 6.36 g (34%) 1-but-3-enyl-1H-[1,2,3]triazole (b.p. 106–108° C. at 10 mbar) as a colorless liquid.

¹H-NMR (400 MHz, [D₆]-DMSO): J=2.59 (q, 2H, CH₂—CH=CH₂), 4.45 (t, 2H, CH₂-triazole), 5.00–5.06(m, 2H, CH₂—CH=CH₂), 5.76 (m, 1H, CH₂—CH=CH₂), 7.70 (s, 1H, triazole), 8.10 (s, 1H, triazole).

ii) 4-(4-[1,2,3]Triazol-1-yl-but-1-enyl)-phenol

A mixture of 3.00 g (24.4 mmol) 1-but-3-enyl-1H-[1,2,3]triazole, 6.79 g (20.3 mmol) tert-Butyl-(4-iodo-phenoxy)-dimethyl-silane, 1.07 g (4.06 mmol) triphenylphosphine, 0.685 g (3.05 mmol) palladium(II)acetate and 56 ml triethylamine was heated to reflux for 24 h. The reaction mixture was cooled to r.t., evaporated, stirred with ice and adjusted to pH=1 by addition of conc. HCl. The organic material was collected with ethyl acetate/dichloromethane 1:2, the organic phase dried over sodium sulfate and evaporated. The residue was stirred with X ml 1M solution of tetrabutylammonium fluoride solution in THF at 28° C. for 3 h. After removal of THF, the residue was dissolved in dichloromethane, washed with water, evaporated and purified by chromatography on silica gel (ethyl acetate/n-heptane 5:1). The product containing fractions were collected, evaporated and stirred with little ethyl acetate/n-heptane 3:1 to yield 1.53 g (29%).

MS: M=216.3 (ESI+).

¹H-NMR(400 MHz, D₆-DMSO): δ=2.69 (q, 2H, CH₂—CH=CH—Ar), 4.49 (t, 2H, CH₂-triazole), 5.97 (dt, 1H, CH=CH—Ar), 6.28 (d, 1H, CH=CH—Ar), 6.68 (d, 2H, 2'-/6'-H), 7.14 (d, 2H, 3'-/5'-H), 7.69 (s, 1H, triazole), 8.12 (s, 1H, triazole), 9.42 (s, 1H, OH).

iii) 1-[4-(4-{2-[2-(4-Pentafluorosulfanyl-phenyl)-vinyl]-oxazol-4-ylmethoxy}-phenyl)-but-3-enyl]-1H-[1,2,3]triazole 13 mg (0.50 mmol) 95% sodium hydride were given to a solution of 108 mg (0.50 mmol) 4-(4-[1,2,3]triazol-1-yl-but-1-enyl)-phenol in 4.0 ml DMF and stirred for 15 min. 173 mg (0.50 mmol) 4-chloromethyl-2-[2-(4-pentafluorosulfanyl-phenyl)-vinyl]-oxazole were added and stirring continued at r.t. overnight. After addition of 10 ml water the resulting precipitate was collected, washed with water (2×10 ml), methanol (2×10 ml), diethyl ether and dried in vacuum at 40° C. to yield 225 mg (86%) of product.

MS: M=525.4 (ESI+).

¹H-NMR(400 MHz, D₆-DMSO): δ=2.73 (dt, 2H, CH₂—CH=CHAr), 4.51 (t, 2H, CH₂-triazole), 5.02 (s, 2H, OCH₂-oxazole), 6.08 (dt, 1H, CH=CH—Ar), 6.35 (d, 1H, CH=CH—Ar), 6.98 (d, 2H, 3'-/5'-H—Ar), 7.30 (d, 2H; 2H, 2'-/6'-H—Ar) 7.36 (d, 1H, vinyl-H), 7.62 (d, 1H, vinyl-H), 7.70 (s, 1H, triazole), 7.92 (m, 4H, ArSF₅), 8.13 (s, 1H, triazole), 8.25 (s, 1H, oxazole).

EXAMPLE 13

1-[4-(4-{2-[2-(4-Pentafluorosulfanyl-phenyl)-vinyl]-oxazol-4-ylmethoxy}-phenyl-but-3-ynyl]-1H-[1,2,3] triazole i) 1-But-3-ynyl-1H-[1,2,3]triazole

But-3-yn-1-ol (49.57 g, 707.2 mmol) and triethylamine (107.7 mL, 777 mmol, dried over KOH) were dissolved in dry dichloromethane (500 mL) under a nitrogen atmosphere and cooled to 0° C. Methanesulfonyl chloride (54.8 mL, 708 mmol, dissolved in 500 mL of dry dichloromethane was added within 90 minutes while keeping the temperature below 5° C. The mixture was stirred for 3.5 hours at room temperature, then poured onto 2.5 L of ice water. The organic phase was separated and washed with 2×500 mL of water and 1×250 mL of brine and dried over sodium sulfate. The volatiles were removed to yield 94.18 g of the methane sulfonate (631.2 mmol, 89.2%) as a yellow liquid.

A suspension of NaOH (37.86 g, 946.5 mmol), sodium iodide (94.65 g, 631.5 mmol) and 1H-[1,2,3]Triazole (61.03 g, 883.6 mmol) in 2-methyl-2-butanol (750 mL) was refluxed for 1 h under an inert atmosphere. After cooling to room temperature the methane sulfonate (94.18 g, 631.2 mmol) was added within 5 minutes. The resulting suspension was then heated to reflux for 3 hours, cooled to room temperature and concentrated on a rotary evaporator at 45° C.

Water (500 mL) and dichloromethane (1 L) were added and the organic phase was separated, dried over sodium sulfate and the volatiles removed at 30° C. The residue was distilled at 1 mmHg. A forerun was collected at 20–70° C. The main fraction distilled at 123–129° C. as a colorless, turbid liquid. After filtration over Celite (filtration over a pad of diatomite) 1-But-3-ynyl-1H-[1,2,3]triazole was obtained as a colorless liquid (29.8 g, 40%).

The content according to GC/FID was >98%.

¹H-NMR (CDCl₃) δ=2.05 (t, 1H, C≡CH), 2.75 (dt, 2H, CH₂—C≡CH), 4.5 (t, 2H, CH₂-triazole), 7.65 (s, 1H, triazole), 7.70 (s, 1H, triazole).

ii) 1-{4-[4-(tert-Butyl-dimethyl-silanyloxy)-phenyl]-but-3-ynyl}-1H-[1,2,3]triazole A solution of 1.94 g (16.1 mmol) 1-but-3-ynyl-1H-[1,2,3]triazole in 14 ml THF were added dropwise at 0° C. to a suspension of 3.35 g (10.0 mmol) tert-butyl-(4-iodo-phenoxy)-dimethyl-silane, 190 mg (1.00 mmol) Cu(I)I and 562 mg (0.80 mmol) Pd(PPh₃)₄ in 16 ml THF, followed by addition of 7.1 ml (50 mmol) diisopropylamine. The mixture was stirred at room temperature for 20 h, 30 ml water added, extracted twice with dichloromethane and the organic phase dried over sodium sulphate. After evaporation and purification by chromatography on silica gel (ethyl acetate/n-heptane 1:1) 2.80 g (85%) were obtained.

MS: M=328.3 (APCI+).

¹H-NMR(400 MHz, D₆-DMSO): δ=0.18 (s, 6H, SiCH₃), 0.94 (s, 9H, C(CH₃)₃), 2.99 (t, 2H, CH₂—C≡CH), 4.59 (t, 2H, CH₂-triazole), 6.81 (d, 2H, 3'-/5'-H), 7.21 (d, 2H, 2'-/6'-H), 7.74 (s, 1H, triazole), 8.20 (s, 1H, triazole).

iii) 4-(4-[1,2,3]Triazol-1-yl-but-1-ynyl)-phenol

A mixture of 1.00 g (3.05 mmol) 1-{4-[4-(tert-butyl-dimethyl-silanyloxy)-phenyl]-but-3-ynyl}-1H-[1,2,3]triazole and 3.05 ml 1M tetrabutylammonium fluoride solution in THF was stirred for 3 h. After evaporation the residue was dissolved in dichloromethane and washed with water that was acidified by acetic acid. The organic phase was dried, evaporated and purified by chromatography on silica gel (ethyl acetate) to give 612 mg (94%) of the title compound.

MS: M=214.1 (ESI+), 212.0(ESI−).

¹H-NMR(400 MHz, D₆-DMSO): δ=2.97 (t, 2H, CH₂—C≡CH), 4.58 (t, 2H, , CH₂-triazole), 7 (d, 2H, 2'-/6'-H), 7.13 (d, 2H, 3'-/5'-H), 7.74 (s, 1H, triazole), 8.19 (s, 1H, triazole), 9.76 (s, 1H, OH).

iv) 1-[4-(4-{2-[2-(4-Pentafluorosulfanyl-phenyl)-vinyl]-oxazol-4-ylmethoxy}-phenyl)-but-3-ynyl]-1H-[1,2,3]triazole 13 mg (0.50 mmol) 95% sodium hydride were given to a solution of 107 mg (0.50 mmol) 4-(4-[1,2,3]triazol-1-yl-but.1-ynyl)-phenol in 4.0 ml DMF and stirred for 15 min. 173 mg (0.50 mmol) 4-chloromethyl-2-[2-(4-pentafluorosulfanyl-phenyl)-vinyl]-oxazole were added and stirring continued at r.t. overnight. After addition of 10 ml water the resulting precipitate was collected, washed with water (2×10 ml), methanol (2×10 ml), diethyl ether and dried in vacuum to yield 182 mg (70%) of product.

MS: M=523.0 (ESI+), 545.0(M+Na+, ESI+).
$^1$H-NMR(400 MHz, D$_6$-DMSO): δ=3.00 (t, 2H, CH$_2$—C≡CH), 4.60 (t, 2H, CH$_2$-triazole), 5.04 (s, 2H, OCH$_2$-oxazole), 7.01 (d, 2H, 3'-/5'-H—Ar), 7.27 (d, 2H; 2H, 2'-/6'-H—Ar) 7.35 (d, 1H, vinyl-H), 7.61 (d, 1H, vinyl-H), 7.75 (s, 1H, triazole), 7.94 (m, 4H, ArSF$_5$), 8.21 (s, 1H, triazole), 8.27 (s, 1H, oxazole).

EXAMPLE 14

N-(2-[1,2,3]Triazol-1-yl-ethyl)-4-{2-[2-(4-pentafluorosulfanyl-phenyl)-vinyl]-oxazol-4-ylmethoxy}-benzenesulfonamide i) [1,2,3]Triazol-1-yl-acetonitrile

A mixture of 40 g (0.58 mol) 1H-[1,2,3]triazole and 94.34 g (0.29 mol) cesium carbonate in 500 ml butanone was stirred at 60° C. for 30 min, then 69.5 g (0.58 mol) bromoacetonitrile were added and stirring at 60° C. continued for another 5 hours. The solvent was evaporated, the residue mixed with water, and extracted thrice with 150 ml ethyl acetate. The combined organic phases were dried, evaporated, and the residue distilled in vacuo. The fraction distilling at 108° C. (0.03 mbar) was collected to yield 28.15 g (45%) [1,2,3]triazol-1-yl-acetonitrile as red oil.

$^1$H-NMR(400 MHz, D$_6$-DMSO): δ=5.82 (s, 2H, CH$_2$), 7.85 (s, 1H, triazole), 8.29 (s, 1H, triazole).

ii) 2-[1,2,3]Triazol-1-yl-ethylamine

A solution of 7.5 g (69 mmol) [1,2,3]triazol-1-yl-acetonitrile in liquid ammonia containing THF was hydrogenated over 5 g Raney nickel at 120 bar and 90° C. The catalyst was filtered off, the solvent concentrated and the residue distilled. The fraction distilling at 91° C. (0.03 mbar) was collected to yield 4.3 g (55%) 2-[1,2,3]triazol-1-yl-ethylamine as colorless oil.

$^1$H-NMR(400 MHz, D$_6$-DMSO): δ=2.96 (t, 2H, CH$_2$), 3.07 (br, 2H, NH$_2$), 4.33 (t, 2H, CH$_2$), 7.71 (s, 1H, triazole), 8.10 (s, 1H, triazole).

iii) 4-Hydroxy-benzenesulfonylchloride 5 g (21.5 mmol) sodium 4-hydroxy-benzenesulfonate dihydrate were suspended in 50 ml toluene and refluxed for 2 hours using a Dean-Stark trap (a water separator used in chemical reactions). The solvent was evaporated, replaced by 12.8 g (108 mmol) thionyl chloride and 160 mg DMF and the mixture stirred for 4 hours at 60° C. and over night at room temperature. After evaporation, the residue was quenched with ice water, extracted thrice with dichloromethane and the extracts died and evaporated. Yield 4.78 g (quant.) raw product as white gum.

$^1$H-NMR(400 MHz, D$_6$-DMSO): δ=6.71 (d, 2H, Ar—H), 7.43 (d, 2H, Ar—H), 12.9 (br, 1H, OH).

iv) 4-Hydroxy-N-(2-[1,2,3]triazol-1-yl-ethyl)-benzenesulfonamide

To a mixture of 9.31 g (83.1 mmol) 2-[1,2,3]triazol-1-yl-ethylamine and 13.96 g (166 mmol) sodium hydrogencarbonate in 320 ml THF was added dropwise a solution of 16.0 g (83.1 mmol) 4-hydroxy-benzenesulfonylchloride in 160 ml THF at room temperature. Stirring was continued at 80° C. for 4 hours, then the solvent was evaporated and the residue triturated with 100 ml water to leave 16.05 g (72%) title compound as white solid melting at 220–223° C. (dec).

MS: M=269.1(API+)
$^1$H-NMR(400 MHz, D$_6$-DMSO): δ=3.15 (t, 2H, CH$_2$), 4.42 (t, 2H, CH$_2$), 6.90 (d, 2H, Ar—H), 7.60 (d, 2H, Ar—H), 7.64 (br, 1H, NH), 7.68 (s, 1H, triazole), 8.06 (s, 1H, triazole), 10.3 (br, 1H, OH).

v) N-(2-[1,2,3]Triazol-1-yl-ethyl)-(4-{2-[(E)-2-(4-pentafluorosulfanyl-phenyl)-vinyl]-oxazol-4-ylmethoxy}-benzenesulfonamide A mixture of 145 mg (0.54 mmol) 4-hydroxy-N-(2-[1,2,3]triazol-1-yl-ethyl)-benzenesulfon-amide and 117 mg (0.36 mmol) cesium carbonate in 10 ml butanone was stirred at 60° C. for 30 min, then 207 mg (0.6 mmol) 4-chloromethyl-2-[2-(4-pentafluorosulfanyl-phenyl)-vinyl]-oxazole and 100 mg (0.6 mmol) potassium iodide were added and stirring at 60° C. continued overnight. After evaporation, the residue was mixed with 15 ml water and extracted thrice with 15 ml ethyl acetate. The combined extracts were dried, evaporated and the product purified on silica. Elution with heptane/ethyl acetate 1:5 yielded 148 mg (43%) N-(2-[1,2,3]triazol-1-yl-ethyl)-(4-{2-[(E)-2-(4-pentafluorosulfanyl-phenyl)-vinyl]-oxazol-4-ylmethoxy}-benzene-sulfonamide as white solid melting at 170–172° C.

MS: M=578.0(ESI+) $^1$H-NMR(400 MHz, D$_6$-DMSO): δ=3.18 (t, 2H, CH$_2$), 4.44 (t, 2H, CH$_2$), 5.16 (s, 2H, OCH$_2$), 7.24 (d, 2H, Ar—H), 7.37 (d, 1H, vinyl), 7.64 (d, 1H, vinyl), 7.73 (m, 3H, 2Ar—H+triazol), 7.78 (t, 1H, NH), 7.95 (m, 4H, Ar—H), 8.08 (s, 1H, triazole), 8.33 (s, 1H, oxazole).

EXAMPLE 15

1-[3-(4-{2-[2-(4-Pentafluorosulfanyl-phenyl)-vinyl]-oxazol-4-ylmethoxy}-phenoxy)-propyl]-1H-[1,2,3]triazole 14 mg (0.55 mmol) 95% sodium hydride were given to a solution of 110 mg (0.50 mmol) 4-(3-[1,2,3]triazol-1-yl-propoxy)-phenol in 4.0 ml DMF and stirred for 15 min. 173 mg (0.50 mmol) 4-chloromethyl-2-[2-(4-pentafluorosulfanyl-phenyl)-vinyl]-oxazole were added and stirring continued at r.t. overnight. After addition of 8 ml water the resulting precipitate was collected , washed with water (2×10 ml), methanol/water 1:1 (2×10 ml), ethyl acetate/n-heptane 1:2, a small amount of diethyl ether and dried to yield 233 mg (88%) of a slightly yellow powder.

MS: M=529.0 (ESI+), 550.9(M+Na+, ESI+).
$^1$H-NMR(400 MHz, D$_6$-DMSO): δ=2.26 (quintet, 2H, CH$_2$—CH$_2$-triazole), 3.90 (t, 2H, OCHH$_2$ CH$_2$—CH$_2$-triazole), 4.55 (t, 2H, CH$_2$-triazole), 4.96 (s, 2H, OCH$_2$-oxazole), 6.86 (d, 2H, Ar—H), 6.97 (d, 2H, Ar—H) 7.35 (d, 1H, vinyl-H), 7.61 (d, 1H, vinyl-H), 7.73 (s, 1H, triazole), 7.94 (m, 4H, ArSF$_5$), 8.15 (s, 1H, triazole), 8.23 (s, 1H, oxazole).

$^1$H-NMR (400 MHz, CDCl$_3$): 2.67 (m, 2H), 4.18 (d, 2H), 4.47 (t, 2H), 5.87 (m, 1H), 6.17–6.24 (m, 2H), 6.58 (d, 2H), 7.08 (d, 2H), 7.31 (d, 1H), 7.55 (d, 1H), 7.69 (s, 1H), 7.92 (s, 4H), 7.99 (s, 1H), 8.11 (s, 1H)

EXAMPLE 16

[4-(4-[1,2,3]Triazol-1-yl-butyl)-phenyl]-{2-[2-(4-pentafluorosulfanyl-phenyl)-vinyl]-oxazol-4-ylmethyl}-amine i) [4-(4-[1,2,3]Triazol-1-yl-butyl)-phenyl]-carbamic acid tert-butyl ester To a solution of 10.0 g (46.2 mmol) 4-(4-[1,2,3]triazol-1-yl-butyl)-phenylamine in 100 ml THF were added at 0° C. 92.5 ml of a 1 M solution of bis-trimethylsilyl lithiumamide in THF and thereafter at room temperature a solution of 9.08 g (41.6 mmol) di-tert-butyl dicarbonate in THF. After stirring for 30 min, the mixture was quenched with ammonium chloride solution and extracted with ethyl acetate. The extract was dried, evaporated and the residue purified on silica. Elution with ethyl acetate yielded 12.0 g (82%) title compound as slightly yellow crystals.

ii) [4-(4-[1,2,3]Triazol-1-yl-butyl)-phenyl]-{2-[2-(4-pentafluorosulfanyl-phenyl)-vinyl]-oxazol-4-ylmethyl}-carbamic acid tert-butyl ester 40 mg (1.00 mmol) 60% sodium hydride were given at 0° C. to a solution of 316 mg (1.00 mmol) 4-(4-[1,2,3]triazol-1-yl-butyl)-phenyl]-carbamic acid tert-butyl ester in 5.0 ml DMF and stirred for 15 min. at room temperature. 346 mg (1.00 mmol) 4-Chloromethyl-2-[2-(4-pentafluorosulfanyl-phenyl)-vinyl]-oxazole were added and stirring continued at 25° C. for 16 h. After careful addition of 5 ml water, the mixture was poured into 45 ml water, stirred for 30 min. and the formed precipitate isolated by filtration, washed with water, water/methanol 1:1, and n-heptane, and dried in vacuo at 40° C. to yield 490 mg (78%) [4-(4-[1,2,3]triazol-1-yl-butyl)-phenyl]-{2-[2-(4-pentafluorosulfanyl-phenyl)-vinyl]-oxazol-4-ylmethyl}-carbamic acid tert-butyl ester.

iii) 4-(4-[1,2,3]Triazol-1-yl-butyl)-phenyl]-{2-[2-(4-pentafluorosulfanyl-phenyl)-vinyl]-oxazol-4-ylmethyl}-amine A solution of 450 mg (0.72 mmol) [4-(4-[1,2,3]triazol-1-yl-butyl)-phenyl]-{2-[2-(4-pentafluorosulfanyl-phenyl)-vinyl]-oxazol-4-ylmethyl}-carbamic acid tert-butyl ester in 4 ml dichloromethane and 4 ml trifluoroacetic acid was stirred at r.t. for 1 h. Water was added and the mixture neutralized with solid sodium carbonate. The organic phase was separated, washed with water, dried over sodium sulfate and evaporated. The residue was stirred with a little isopropanol, the crystallized material isolated by filtration, washed with ether and dried to give 100 mg (27%) of product.

MS: M=526.0 (ESI+), 524.1(ESI−).

$^1$H-NMR(400 MHz, D$_6$-DMSO): δ=1.43 (quintet, 2H, CH$_2$—CH$_2$—Ar), 1.79 (quintet, 2H, CH$_2$—CH$_2$-triazole), 2.43 (t, 2H, CH$_2$—Ar), 4.15 (d, 2H, NHCH$_2$-oxazole), 4.37 (t, 2H, CH$_2$-triazole), 5.84 (t, 1H, NH), 6.56 (d, 2H, 3'-/5'-H—Ar), 6.88 (d, 2H, 2'-/6'-H—Ar) 7.31 (d, 1H, vinyl-H), 7.55 (d, 1H, vinyl-H), 7.70 (s, 1H, triazole), 7.93 (m, 4H, ArSF$_5$), 7.98 (s, 1H, triazole), 8.10 (s, 1H, oxazole).

EXAMPLE 17

1-[4-(4-{2-[2-(4-Pentafluorosulfanyl-phenyl)-vinyl]-oxazol-4-ylmethanesulfonyl}-phenyl)-butyl]-1H-[1,2,3]triazole i) 4-(4-Bromo-benzenesulfonylmethyl)-2-[2-(4-pentafluorosulfanyl-phenyl)-vinyl]-oxazole A solution of 4-chloromethyl-2-[2-(4-pentafluorosulfanyl-phenyl)-vinyl]-oxazole (0.30 g, 1.28 mmol) and sodium 4-bromobenzenesulfinate (0.717 g, 2.57 mmol) in N,N-dimethyl formamide (20 ml) was stirred for 3 h at 60° C. After cooling the mixture was poured onto water, extracted with ethyl acetate (3×50 ml), the combined organic layers were washed with water, dried over sodium sulfate, concentrated in vacuo and crystallized from ether/isohexane yielding 4-(4-bromo-benzenesulfonylmethyl)-2-[2-(4-pentafluorosulfanyl-phenyl)-vinyl]-oxazole as white crystalline product. Yield 0.345 g (51%).

MS: M=531.8 (API+), 529.8(API+).

$^1$H-NMR(400 MHz, CDCl$_3$); δ=4.36 (s, 2H, CH$_2$SO$_2$), 6.90 (d, 1H, vinyl-H), 7.43 (d, 1H, vinyl-H), 7.57 (d, 2H, Ar—Br), 7.69 (m, 4H, Ar—SF$_5$), 7.72 (s, 1H, oxazole-H), 7.77 (d, 2H, Ar—Br).

ii) 1-[4-(4-{2-[2-(4-Pentafluorosulfanyl-phenyl)-vinyl]-oxazol-4-ylmethanesulfonyl}-phenyl)-butyl]-1H-[1,2,3]triazole A solution of 1-but-3-enyl-1H-[1,2,3]triazole (80 mg, 0.65 mmol) in anhydrous THF (5 ml) was treated with 9-BBN (0.5 M in THF, 2.86 ml, 1.43 mmol) at 0° C. and stirred for 2 h at room temperature. This mixture was added to a solution of 4-(4-bromo-benzenesulfonylmethyl)-2-[2-(4-pentafluorosulfanyl-phenyl)-vinyl]-oxazole (345 mg, 0.65 mmol), [Pd(dppf)Cl$_2$] (57 mg, 0.07 mmol) and aqueous cesium carbonate (3M, 0.65 ml, 1.95 mmol) in N,N-dimethyl formamide (4 ml) and stirred for 3 h at 70° C. After cooling to room temperature ethyl acetate (100 ml) was added and the solution washed with water (2×50 ml). The organic layer was concentrated and the crude product purified by flash column chromatography (ethyl acetate) and crystallization from diethyl ether to yield 1-[4-(4-{2-[2-(4-pentafluorosulfanyl-phenyl)-vinyl]-oxazol-4-ylmethanesulfonyl}-phenyl)-butyl]-1H-[1,2,3]triazole as white solid (213 mg, 57%).

MS: M=575.0 (API+), 573.0(API−).

$^1$H-NMR(400 MHz, D$_6$-DMSO): δ=1.54 (quintet, 2H), 1.83 (quintet, 2H), 2.71 (t, 2H, CH$_2$—Ar), 4.39 (t, 2H, CH$_2$-triazole), 4.65 (s, 2H, CH$_2$SO$_2$), 7.27 (d, 1H, vinyl-H), 7.44 (d, 2H, ArSO$_2$), 7.51 (d, 1H, vinyl-H), 7.71 (s, 1H, triazole), 7.72 (d, 2H, ArSO$_2$), 7.92 (s, 4H, ArSF$_5$), 8.00 (s, 1H, triazole), 8.10 (s, 1H, oxazole).

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:
1. The compounds of formula I-A and any pharmaceutically acceptable salt or ester thereof wherein formula I-A is:

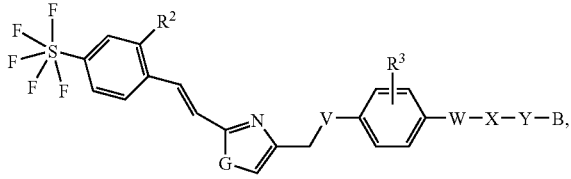

formula I-A wherein:
$R^2$ is hydrogen or fluorine;
$R^3$ is hydrogen, $(C_1-C_3)$alkyl, $(C_1-C_3)$alkoxy or halogen;
G is —O—;
V is —O—;
W is —$CH_2$— or a direct bond;
X is —CH=CH—, —C≡C— or —$CH_2$—;
Y is —$(CH_2)_n$—;
B is selected from the group consisting of:
(a) imidazolyl; which is:
    (1) unsubstituted; or
    (2) once substituted with —C(O)OH; or
    (3) one, two or three times substituted with alkyl, which alkyl is:
        (A) optionally interrupted one, two or three times by —O—, —$S(O)_x$—, —$S(O)_2NH$—, —$NHS(O)_2$—, —C(O)—NH—, —NH—C(O)— or —P(O)($CH_3$)—; and
        (B) unsubstituted or one, two or three times substituted with —OH, —$NH_2$, —C(O)OH, or —P(O)($CH_3$)$_2$; or
    (4) once substituted with —C(O)OH and one, two or three times substituted with alkyl, which alkyl is:
        (A) optionally interrupted one, two or three times by —O—, —$S(O)_x$—, —$S(O)_2NH$—, —$NHS(O)_2$—, —C(O)—NH—, —NH—C(O)— or —P(O)($CH_3$)—; and
        (B) unsubstituted or one, two or three times substituted with —OH, —$NH_2$, —C(O)OH, or —P(O)($CH_3$)$_2$;
(b) pyrazolyl; which is:
    (1) unsubstituted; or
    (2) once substituted with —C(O)OH; or
    (3) one, two or three times substituted with alkyl, which alkyl is:
        (A) optionally interrupted one, two or three times by —O—, —$S(O)_x$—, —$S(O)_2NH$—, —$NHS(O)_2$—, —C(O)—NH—, —NH—C(O)— or —P(O)($CH_3$)—; and
        (B) unsubstituted or one, two or three times substituted with —OH, —$NH_2$, —C(O)OH, or —P(O)($CH_3$)$_2$; or
    (4) once substituted with —C(O)OH and one, two or three times substituted with alkyl, which alkyl is:
        (A) optionally interrupted one, two or three times by —O—, —$S(O)_x$—, —$S(O)_2NH$—, —$NHS(O)_2$—, —C(O)—NH—, —NH—C(O)— or —P(O)($CH_3$)—; and
        (B) unsubstituted or one, two or three times substituted with —OH, —$NH_2$, —C(O)OH, or —P(O)($CH_3$)$_2$;
(c) triazolyl; which is:
    (1) unsubstituted; or
    (2) once substituted with —C(O)OH; or
    (3) one, two or three times substituted with alkyl, which alkyl is:
        (A) optionally interrupted one, two or three times by —O—, —$S(O)_x$—, —$S(O)_2NH$—, —$NHS(O)_2$—, —C(O)—NH—, —NH—C(O)— or —P(O)($CH_3$)—; and
        (B) unsubstituted or one, two or three times substituted with —OH, —$NH_2$, —C(O)OH, or —P(O)($CH_3$)$_2$; or
    (4) once substituted with —C(O)OH and one, two or three times substituted with alkyl, which alkyl is:
        (A) optionally interrupted one, two or three times by —O—, —$S(O)_x$—, —$S(O)_2NH$—, —NHS$(O)_2$—, —C(O)—NH—, —NH—C(O)— or —P(O)($CH_3$)—; and
        (B) unsubstituted or one, two or three times substituted with —OH, —$NH_2$, —C(O)OH, or —P(O)($CH_3$)$_2$; and
(d) tetrazolyl, which is:
    (1) unsubstituted; or
    (2) once substituted with —C(O)OH; or
    (3) one, two or three times substituted with alkyl, which alkyl is:
        (A) optionally interrupted one, two or three times by —O—, —$S(O)_x$—, —$S(O)_2NH$—, —NHS$(O)_2$—, —C(O)—NH—, —NH—C(O)— or —P(O)($CH_3$)—; and
        (B) unsubstituted or one, two or three times substituted with —OH, —$NH_2$, —C(O)OH, or —P(O)($CH_3$)$_2$; or
    (4) once substituted with —C(O)OH and one, two or three times substituted with alkyl, which alkyl is:
        (A) optionally interrupted one, two or three times by —O—, —$S(O)_x$—, —$S(O)_2NH$—, —NHS$(O)_2$—, —C(O)—NH—, —NH—C(O)— or —P(O)($CH_3$)—; and
        (B) unsubstituted or one, two or three times substituted with —OH, —$NH_2$, —C(O)OH, or —P(O)($CH_3$)$_2$;
n is 1, 2 or 3; and
x is 0, 1 or 2.
2. The compounds according to claim 1, wherein:
$R^2$ is fluorine.
3. The compounds according to claim 1, wherein:
$R^2$ is hydrogen.
4. The compounds according to claim 1, wherein:
$R^2$ and $R^3$ are both hydrogen;
—W—X—Y— is —$(CH_2)_4$—; and
B is selected from the group consisting of:
(a) imidazolyl; which is:
    (1) unsubstituted; or
    (2) once substituted with —C(O)OH; or
    (3) one, two or three times substituted with alkyl, which alkyl is:
        (A) optionally interrupted one, two or three times by —O—, —$S(O)_x$—, —$S(O)_2NH$—, —NHS$(O)_2$—, —C(O)—NH—, —NH—C(O) — or —P(O)($CH_3$)—; and
        (B) unsubstituted or one, two or three times substituted with —OH, —$NH_2$, —C(O)OH, or —P(O)($CH_3$)$_2$; or (4) once substituted with —C(O)OH and one, two or three times substituted with alkyl, which alkyl is:
   (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
   (B) unsubstituted or one, two or three times substituted with —OH, —NH$_2$, —C(O)OH, or —P(O)(CH$_3$)$_2$;

(b) pyrazolyl; which is:
   (1) unsubstituted; or
   (2) once substituted with —C(O)OH; or
   (3) one, two or three times substituted with alkyl, which alkyl is:
      (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
      (B) unsubstituted or one, two or three times substituted with —OH, —NH$_2$, —C(O)OH, or —P(O)(CH$_3$)$_2$; or
   (4) once substituted with —C(O)OH and one, two or three times substituted with alkyl, which alkyl is:
      (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
      (B) unsubstituted or one, two or three times substituted with —OH, —NH$_2$, —C(O)OH, or —P(O)(CH$_3$)$_2$;

(c) triazolyl; which is:
   (1) unsubstituted; or
   (2) once substituted with —C(O)OH; or
   (3) one, two or three times substituted with alkyl, which alkyl is:
      (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
      (B) unsubstituted or one, two or three times substituted with —OH, —NH$_2$, —C(O)OH, or —P(O)(CH$_3$)$_2$; or
   (4) once substituted with —C(O)OH and one, two or three times substituted with alkyl, which alkyl is:
      (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
      (B) unsubstituted or one, two or three times substituted with —OH, —NH$_2$, —C(O)OH, or —P(O)(CH$_3$)$_2$; and (d) tetrazolyl, which is:
   (1) unsubstituted; or
   (2) once substituted with —C(O)OH; or
   (3) one, two or three times substituted with alkyl, which alkyl is:
      (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
      (B) unsubstituted or one, two or three times substituted with —OH, —NH$_2$, —C(O)OH, or —P(O)(CH$_3$)$_2$; or (4) once substituted with —C(O)OH and one, two or three times substituted with alkyl, which alkyl is:
   (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
   (B) unsubstituted or one, two or three times substituted with —OH, —NH$_2$, —C(O)OH, or —P(O)(CH$_3$)$_2$.

5. The compounds according to claim 1, wherein:
$R^2$ and $R^3$ are both hydrogen;
—W—X—Y— is —(CH$_2$)$_4$—; and
B is selected from the group consisting of:
   (a) an imidazolyl ring, which is: (1) unsubstituted, or (2) once substituted with 2-(2-hydroxyethoxy)ethyl, 1-hydroxyethyl, 2-hydroxyethyl, 2-(2-methoxy-ethoxy)-ethyl, hydroxymethyl, 2-methanesulfinyl-ethyl, 2-methanesulfonyl-ethyl, dimethyl-phosphinoylmethyl, methoxymethyl, carboxymethyl, 2-carboxyethyl, aminomethyl, 1-aminoethyl, or 2-aminoethyl;
   (b) a triazolyl ring, which is: (1) unsubstituted, or (2) once substituted with 2-(2-hydroxyethoxy)ethyl, 1-hydroxyethyl, 2-hydroxyethyl, 2-(2-methoxy-ethoxy)-ethyl, hydroxymethyl, 2-methanesulfinyl-ethyl, 2-methanesulfonyl-ethyl, dimethyl-phosphinoylmethyl, methoxymethyl, carboxymethyl, 2-carboxyethyl, aminomethyl, 1-aminoethyl, or 2-aminoethyl; and
   (c) a tetrazolyl ring, which is: (1) unsubstituted, or (2) once substituted with 2-(2-hydroxyethoxy)ethyl, 1-hydroxyethyl, 2-hydroxyethyl, 2-(2-methoxy-ethoxy)-ethyl, hydroxymethyl, 2-methanesulfinyl-ethyl, 2-methanesulfonyl-ethyl, dimethyl-phosphinoylmethyl, methoxymethyl, carboxymethyl, 2-carboxyethyl, aminomethyl, 1-aminoethyl, or 2-aminoethyl.

6. The compounds according to claim 5 selected from the group consisting of:
   4-[4-(4-Imidazol-1-yl-butyl)-phenoxymethyl]-2-[2-(4-pentafluorosulfanyl-phenyl)-vinyl]-oxazole;
   2-{1-[4-(4-{2-[(E)-2-(-4-Pentafluorosulfanyl-phenyl)-vinyl]-oxazol-4-ylmethoxy}-phenyl)-butyl]-1H-imidazol-2-yl}-ethanol;
   1-[4-(4-{2-[(E)-2-(-4-Pentafluorosulfanyl-phenyl)-vinyl]-oxazol-4-ylmethoxy}-phenyl)-butyl]-1H-[1,2,3]triazole;
   4-[4-(4-{2-[(E)-2-(-4-Pentafluorosulfanyl-phenyl)-vinyl]-oxazol-4-ylmethoxy}-phenyl)-butyl]-1H-[1,2,3]triazole;
   5-[4-(4-{2-[(E)-2-(-4-Pentafluorosulfanyl-phenyl)-vinyl]-oxazol-4-ylmethoxy}-phenyl)-butyl]-2H-tetrazole;
   2-{5-[4-(4-{2-[2-(4-Pentafluorosulfanyl-phenyl)-vinyl]-oxazol-4-ylmethoxy}-phenyl)-butyl]-tetrazol-1-yl}-ethanol; and
   2-{5-[4-(4-{2-[2-(4-Pentafluorosulfanyl-phenyl)-vinyl]-oxazol-4-ylmethoxy}-phenyl)-butyl]-tetrazol-2-yl}-ethanol.

7. The compounds according to claim 1, wherein:
$R^2$ and $R^3$ are both hydrogen;
—W—X—Y— is —CH=CH—CH$_2$—; —CH=CH—(CH$_2$)$_2$—;
—CH$_2$—CH=CH—CH$_2$—; or —C≡C—(CH$_2$)$_2$—; and B is selected from the group consisting of:
(a) imidazolyl; which is:
(1) unsubstituted; or
(2) once substituted with —C(O)OH; or
(3) one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$; or
(4) once substituted with —C(O)OH and one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and (B) unsubstituted or one, two or three times substituted with —OH, —NH$_2$, —C(O)OH, or —P(O)(CH$_3$)$_2$;
(b) pyrazolyl; which is:
(1) unsubstituted; or
(2) once substituted with —C(O)OH; or
(3) one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$; or
(4) once substituted with —C(O)OH and one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$;
(c) triazolyl; which is:
(1) unsubstituted; or
(2) once substituted with —C(O)OH; or
(3) one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$; or
(4) once substituted with —C(O)OH and one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$; and
(d) tetrazolyl, which is:
(1) unsubstituted; or
(2) once substituted with —C(O)OH; or
(3) one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$; or
(4) once substituted with —C(O)OH and one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$.

8. The compounds according to claim 1, wherein
R$^2$ and R$^3$ are both hydrogen;
—W—X—Y— is —CH=CH—(CH$_2$)$_2$—;
or —C≡C—(CH$_2$)$_2$—; and
B is triazolyl.

9. The compounds according to claim 8 selected from the group consisting of:
1-[4-(4-{2-[2-(4-Pentafluorosulfanyl-phenyl)-vinyl]-oxazol-4-ylmethoxy}-phenyl)-but-3-enyl]-1H-[1,2,3]triazole; and
1-[4-(4-{2-[2-(4-Pentafluorosulfanyl-phenyl)-vinyl]-oxazol-4-ylmethoxy}-phenyl)-but-3-ynyl]-1H-[1,2,3]triazole;.

10. The compounds according to claim 1, wherein:
R$^2$ and R$^3$ are both hydrogen;
—W—X—Y— is —(CH$_2$)$_4$—;
B is selected from the group consisting of:
(a) imidazolyl; which is:
(1) unsubstituted; or
(2) once substituted with —C(O)OH; or
(3) one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$; or
(4) once substituted with —C(O)OH and one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$;
(b) pyrazolyl; which is:
(1) unsubstituted; or
(2) once substituted with —C(O)OH; or
(3) one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and (B) unsubstituted or one, two or three times substituted with —OH, —NH$_2$, —C(O)OH, or —P(O)(CH$_3$)$_2$; or
(4) once substituted with —C(O)OH and one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$;
(c) triazolyl; which is:
(1) unsubstituted; or
(2) once substituted with —C(O)OH; or
(3) one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$; or
(4) once substituted with —C(O)OH and one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$; and
(d) tetrazolyl, which is:
(1) unsubstituted; or
(2) once substituted with —C(O)OH; or
(3) one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$; or
(4) once substituted with —C(O)OH and one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$; and
x is 0, 1 or 2.
11. The compounds according to claim 1, wherein:
R$^2$ and R$^3$ are both hydrogen;
—W—X—Y— is —CH=CH—CH$_2$—, —CH=CH—(CH$_2$)$_2$—, —CH$_2$—CH=CH—CH$_2$—, or —C≡C—(CH$_2$)$_2$—;
B is selected from the group consisting of:
(a) imidazolyl; which is:
(1) unsubstituted; or
(2) once substituted with —C(O)OH; or
(3) one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$; or
(4) once substituted with —C(O)OH and one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$;
(b) pyrazolyl; which is:
(1) unsubstituted; or
(2) once substituted with —C(O)OH; or
(3) one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$; or
(4) once substituted with —C(O)OH and one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$;
(c) triazolyl; which is:
(1) unsubstituted; or
(2) once substituted with —C(O)OH; or
(3) one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$; or
(4) once substituted with —C(O)OH and one, two or three times substituted with alkyl, which alkyl is:
(A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
(B) unsubstituted or one, two or three times substituted with —OH, —NH$_2$, —C(O)OH, or —P(O)(CH$_3$)$_2$; and (d) tetrazolyl, which is:
  (1) unsubstituted; or
  (2) once substituted with —C(O)OH; or
  (3) one, two or three times substituted with alkyl, which alkyl is:
    (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
    (B) unsubstituted or one, two or three times substituted with —OH, —NH$_2$, —C(O)OH, or —P(O)(CH$_3$)$_2$; or
  (4) once substituted with —C(O)OH and one, two or three times substituted with alkyl, which alkyl is:
    (A) optionally interrupted one, two or three times by —O—, —S(O)$_x$—, —S(O)$_2$NH—, —NHS(O)$_2$—, —C(O)—NH—, —NH—C(O)— or —P(O)(CH$_3$)—; and
    (B) unsubstituted or one, two or three times substituted with —OH, —NH$_2$, —C(O)OH, or —P(O)(CH$_3$)$_2$; and x is 0, 1 or 2.

12. The compounds according to claim 1, wherein:

R$^2$ and R$^3$ are both hydrogen;

—W—X—Y— is —CH=CH—(CH$_2$)$_2$—, or —C≡C—(CH$_2$)$_2$—; and

B is triazolyl.

13. The compounds according to claim 1, wherein:

R$^2$ and R$^3$ are both hydrogen;

—W—X—Y— is —(CH$_2$)$_4$—; and

B is triazolyl.

14. The process for the manufacture of the compounds according to claim 1, wherein:

a) a compound of formula II-A

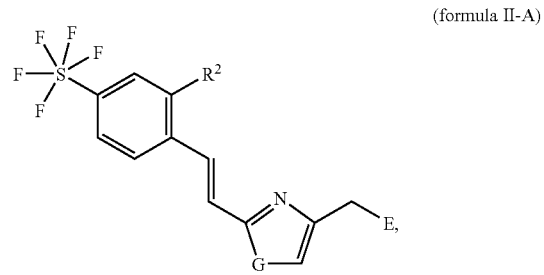

(formula II-A)

wherein R$^2$ and G have the meanings provided in claim 1, and E denotes a suitable leaving group, is reacted with a compound of formula III-A

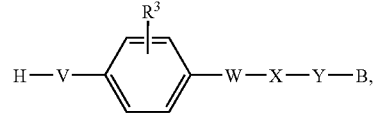

(formula III-A)

wherein R$^3$, V, W, X, Y and B have the meanings provided in claim 1;

b) a protecting group, if present to protect the heteroatoms in the imidazole-, pyrazole-, triazole- or tetrazole ring of "B" from undesired side reactions is cleaved to give a compound of formula I-A;

c) said compound of formula I-A is isolated from the reaction mixture; and d) if desired is turned into a pharmaceutically acceptable salt or ester.

15. A pharmaceutical composition comprising, a therapeutically effective amount of a compound of claim 1 and a pharmaceutically acceptable vehicle.

* * * * *